US008404927B2

(12) United States Patent
Allen et al.

(10) Patent No.: US 8,404,927 B2
(45) Date of Patent: Mar. 26, 2013

(54) **DOUBLE-STRANDED RNA STABILIZED *IN PLANTA***

(75) Inventors: Edwards Allen, O'Fallon, MO (US);
Larry A. Gilbertson, Chesterfield, MO (US); Elysia K. Krieger, Kirkwood, MO (US); James K. Roberts, Chesterfield, MO (US); Jeffrey M. Staub, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/453,155

(22) Filed: Jun. 13, 2006

(65) Prior Publication Data

US 2007/0011775 A1    Jan. 11, 2007

Related U.S. Application Data

(63) Continuation-in-part of application No. 11/303,745, filed on Dec. 15, 2005.

(60) Provisional application No. 60/638,256, filed on Dec. 21, 2004, provisional application No. 60/639,094, (Continued)

(51) Int. Cl.
*A01H 1/00* (2006.01)
*C12N 15/82* (2006.01)
*C07H 21/04* (2006.01)

(52) U.S. Cl. ........ 800/286; 800/285; 800/279; 536/24.5

(58) Field of Classification Search .................. None
See application file for complete search history.

(56) References Cited

U.S. PATENT DOCUMENTS

| | | | |
|---|---|---|---|
| 6,506,559 B1 | 1/2003 | Fire et al. | |
| 7,612,194 B2 | 11/2009 | Andersen et al. | |
| 7,618,814 B2 * | 11/2009 | Bentwich | 435/320.1 |
| 7,754,697 B2 | 7/2010 | Graham et al. | |
| 2003/0150017 A1 * | 8/2003 | Mesa et al. | 800/279 |
| 2003/0175965 A1 | 9/2003 | Lowe et al. | |
| 2004/0053876 A1 * | 3/2004 | Turner et al. | 514/44 |
| 2005/0095199 A1 * | 5/2005 | Whyard et al. | 424/9.2 |
| 2006/0021087 A1 | 1/2006 | Baum et al. | |
| 2006/0035344 A1 * | 2/2006 | Pachuk et al. | 435/91.1 |
| 2006/0272049 A1 * | 11/2006 | Waterhouse et al. | 800/279 |
| 2007/0124836 A1 | 5/2007 | Baum et al. | |
| 2009/0307803 A1 | 12/2009 | Baum et al. | |
| 2010/0192265 A1 | 7/2010 | Andersen et al. | |

FOREIGN PATENT DOCUMENTS

| | | |
|---|---|---|
| CA | 2582550 | 5/2006 |
| WO | WO 01/34815 | 5/2001 |
| WO | WO 01/37654 | 5/2001 |
| WO | WO 01/37654 | 7/2001 |
| WO | WO 02/46432 | 6/2002 |
| WO | WO 03/004644 | 1/2003 |
| WO | WO 2005/019408 | 3/2005 |
| WO | WO 2005/049841 | 6/2005 |
| WO | WO2005/110068 | * 11/2005 |
| WO | WO 2005/110068 | 11/2005 |
| WO | WO 2006/046148 | 5/2006 |
| WO | WO 2007/083193 | 7/2007 |

OTHER PUBLICATIONS

Allan et al. 2005, Physiol. Genomics 22:128-138.*
Xu-Gang Xia, Multiple shRNAs expressed by an individual pol II promoter, BioTechniques, Jul. 2006, vol. 41 (1): 64-68.
3rd party submission in European Patent Application No. EP 98964202.0 inculding reference D1 Huntley et al. (1993) J. Virol., 74:2445-2452.
Hjalt et al., Bulged-out nucleotides in an antisense RNA are required for rapid target RNA binding in vitro and inhibition in vivo, Nucl. Acids Res. 1995, vol. 23, No. 4, pp. 580-587.
Hjalt et al., Bulged-out nucleotides protect an antisense RNA from RNase III cleavage, Nucl. Acids Res. 1995, vol. 23, No. 4, pp. 571-579.
Urwin et al., Ingestion of Double-Stranded RNA by Preparasitic Juvenile Cyst Nematodes Leads to RNA Interference, MPMI. 2002, vol. 15, No. 8, pp. 747-752 (see 748-751).
Xie et al., Dicer-Like 4 functions in trans-acting small interfering RNA biogenesis and vegetative phase change in Arabidopsis thaliana, Sep. 6, 2005, vol. 102, pp. 12984-12989.
Khvorova et al., Functional siRNAs and miRNAs Exhibit Strand Bias, Cell. Oct. 17, 2003, vol. 115, pp. 209-216.
Hanawa et al., Phytoalexins from *Pinus strobus* bark infected with pinewood nematode, *Bursaphelenchus xylophilus*, Phytochemistry 2001, vol. 57, pp. 223-228 (see pp. 223-226.).
Adang et al., The reconstruction and expression of a *Bacillus thuringiensis* cryIIIA gene in protoplasts and potato plants, Plant Mol. Biol. 1993, vol. 21, pp. 1131-1145 (see pp. 1140-1142).
Smith, et al., "Total silencing by intron-spliced hairpin RNAs," Nature, 407:319-320 (2000).
Chang, Jinhong et al., "Resistance of Human Hepatitis Delta Virus RNAs to Dicer Activity," *Journal of Virology*, 77(22):11910-11917, XP002532085 (2003).
Baum, James et al., "Control of Coleopteran Insect Pests through RNA Interference," *Nature Biotechnology*, 25(11):1322-1326, XP-002532086 (2007).
Gordon, Karl et al., "RNAi for Insect-Proof Plants," *Nature Biotechnology*, 25(11):1231-1232, XP-002532186 (2007).

(Continued)

*Primary Examiner* — Li Zheng
(74) *Attorney, Agent, or Firm* — SNR Denton US LLP; Timothy K. Ball, Esq.

(57) ABSTRACT

This invention discloses recombinant DNA constructs that transcribe to RNA having improved resistance to a plant RNase III enzyme, and methods for their use in making transgenic plant cells, plants, seeds, and products derived therefrom. Also provided are compositions and methods for imparting to a plant resistance to a pest or pathogen of the plant.

29 Claims, 9 Drawing Sheets

Related U.S. Application Data filed on Dec. 24, 2004, provisional application No. 60/701,124, filed on Jul. 19, 2005, provisional application No. 60/711,834, filed on Aug. 26, 2005, provisional application No. 60/720,005, filed on Sep. 24, 2005, provisional application No. 60/726,106, filed on Oct. 13, 2005, provisional application No. 60/736,525, filed on Nov. 14, 2005.

(56) References Cited

OTHER PUBLICATIONS

Dow et al., "Molecular genetic analysis of V-ATPase function in Drosophila melanogaster," *J. Exp. Biol.*, 200(Pt. 2):237-245, 1997.
Dow, "The multifunctional *Drosophila melanogaster* V-ATPase is encoded by a multigene family," *J. Bioenerg. Biomembr.*, 31(1):75-83, 1999.
GenBank Accession No. AF008922, dated Jun. 17, 1997.
GenBank Accession No. L09234, dated Jun. 12, 1993.
GenPept Accession No. NP_001682, dated May 10, 2002.
Gill et al., "Isolation of the V-ATPase A and c subunit cDNAs from mosquito midgut and Malpighian tubules," *Archives of Insect Biochemistry and Physiology*, 37:80-90, 1998.
Graf et al., "Cloning and sequencing of cDNA encoding the putative insect plasma membrance V-ATPase subunit A," *FEBS Letters* 300(2):119-122, 1992.
Llave et al., "Endogenous and silencing-associated small RNAs in plants," *Plant Cell* 14(7):1605-1619, 2002.
Myers et al., "Recombinant dicer efficiently converts large dsRNAs into siRNAs suitable for gene silencing," *Nature Biotechnology* 21(3):324-328, 2003.
McManus et al., "Gene silencing using micro-RNA designed hairpins," *RNA* 8(6):842-850, 2002.
GenBank Accession No. U46682, dated Apr. 25, 1996.
GenBank Accession No. AF025809, dated Jan. 31, 2001.

\* cited by examiner

FIGURE 4

```
                                    2.2 2.4 2.2 3.8
2.7 1.1 2.6 1.9                      C   A   C   G
 G   A   T   C  T A G C C G A A A T T G   T   G   C ─┐
-8.3 sense ΔG                           -10.6 anti-sense ΔG
```

$$-8.3 - (-10.6) = 2.3 \; \Delta\Delta G$$

(SEQ ID NO. 1)

SEQ ID NO. 45

SEQ ID NO. 46

Northerns on individual R0 events for pMON100806

Northerns on individual R0 events for pMON100806

A: two-stem (H-type) pseudoknot

B: three-stem pseudoknot

C: "kissing stem loops"

DOUBLE-STRANDED RNA STABILIZED IN PLANTA

PRIORITY CLAIMS AND REFERENCE TO RELATED APPLICATIONS

This application is a Continuation-in-Part of U.S. patent application Ser. No. 11/303,745, filed 15 Dec. 2005, which claims the benefit of priority to U.S. Provisional Patent Applications 60/638,256, which was filed on 21 Dec. 2004, 60/639,094, which was filed on 24 Dec. 2004, 60/701,124, which was filed on 19 Jul. 2005, 60/711,834, which was filed on 26 Aug. 2005, 60/720,005, which was filed on 24 Sep. 2005, 60/726,106, which was filed on 13 Oct. 2005, and 60/736,525, which was filed on 14 Nov. 2005, incorporated herein by reference.

INCORPORATION OF SEQUENCE LISTINGS

The sequence listing that is contained in the file named "38-21(54482)A.rpt" which is 24 kilobytes (measured in operating system MS-Windows), created on 13 Jun. 2006, and located in computer readable form on a compact disk (CD-R), is filed herewith and incorporated herein by reference. The sequence listings contained in the files "38-15(53429)C.ST25.txt" (file size of 97 kilobytes, recorded on 15 Dec. 2005, and filed with U.S. patent application Ser. No. 11/303,745 on 15 Dec. 2005), "53429A.ST25.txt" (file size of 15 kilobytes, recorded on 21 Dec. 2004, and filed with U.S. Provisional Application 60/638,256 on 21 Dec. 2004), "38-21(53709)B.ST25.txt" (file size of 4 kilobytes, recorded on 23 Dec. 2004, and filed with U.S. Provisional Application 60/639,094 on 24 Dec. 2004), "38-15(53429)B.rpt" (file size of 7 kilobytes, recorded on 19 Jul. 2005, filed with U.S. Provisional Application 60/701,124 on 19 Jul. 2005), "38-15(54068)A.rpt" (file size of 6 kilobytes, recorded on 26 Aug. 2005, filed with U.S. Provisional Application 60/711,834 on 26 Aug. 2005), "38-21(54176)A.rpt" (file size of 29 kilobytes, recorded on 23 Sep. 2005, and filed with U.S. Provisional Application 60/720,005 on 24 Sep. 2005), and "38-21(54232)A.rpt" (file size of 61 kilobytes, recorded on 12 Oct. 2005, and filed with U.S. Provisional Application 60/726,106 on 13 Oct. 2005) are incorporated by reference in their entirety herein.

FIELD OF THE INVENTION

This invention relates generally to stabilization of double-stranded RNA transcribed in a plant cell, and more specifically to recombinant DNA constructs that transcribe to RNA having improved resistance to a plant RNase III enzyme. Constructs of the invention are especially useful in making transgenic plant cells, plants, and seeds having resistance to a plant pest or pathogen.

BACKGROUND OF THE INVENTION

Ribonucleases of the RNase III family are believed to be primarily responsible for the processing of double-stranded RNAs involved in post-transcriptional gene silencing in plants; see, for example, Jones-Rhoades et al. (2006) *Annu. Rev. Plant Biol.*, 57:19-53 for a review of siRNA and mRNA biogenesis in plants. Since the requirements for plant and non-plant ribonucleases are not identical, double-stranded RNA can be designed to be resistant to plant ribonucleases but not to non-plant ribonucleases. In some cases, such as where a double-stranded RNA is to be transcribed in a plant cell but targets a non-plant gene, for example, a gene of a pest or a pathogen of the plant), it can be advantageous for the double-stranded RNA to remain relatively intact (e.g., not substantially processed by Dicer or Dicer-like proteins in planta) until it is taken up or contacted by the pest or pathogen.

This invention provides a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. Constructs of the invention are particularly useful in making transgenic plant cells, plants, and seeds having in their genome a recombinant DNA construct of the invention, which imparts resistance to a pest or pathogen of the plant.

This invention further provides methods of providing a transgenic plant having improved resistance to a pest or pathogen of the plant. The transgenic plant can be directly grown from the transgenic plant cell (e.g., from transformed plant callus), or can be a transgenic progeny plant or seed, including an inbred or hybrid transgenic progeny plant or seed.

This invention further provides a composition for imparting to a plant resistance to a pest or pathogen of the plant, including an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. The composition of the invention optionally includes cells of the plant, an insect control agent; and/or a nematode control agent. Methods for using the composition are also provided.

SUMMARY OF THE INVENTION

This invention discloses recombinant DNA constructs that transcribe to RNA including stabilized double-stranded RNA for silencing a target gene, useful for transforming plant cells, and particularly useful for controlling pests or pathogens (e.g., viruses, bacteria, fungi, and invertebrates such as insects, nematodes, and molluscs) of a plant.

One aspect of this invention provides a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. The stabilizing feature of the RNA is one or more selected from the group consisting of:
  (a) a mismatch in the double-stranded RNA resulting from substitution of a single base for one base in the sense strand of the double-stranded RNA;
  (b) a mismatch in the double-stranded RNA resulting from substitution of two bases for one base in the sense strand of the double-stranded RNA;
  (c) a mismatch in the double-stranded RNA resulting from deletion of a single base in the sense strand of the double-stranded RNA;
  (d) a mismatch in the double-stranded RNA resulting from insertion of three or more non-base-paired bases into the sense strand of the double-stranded RNA;
  (e) a mismatch in the double-stranded RNA resulting from insertion of a non-base-paired segment of at least 3 nucleotides in length in both the sense strand and the anti-sense strand of the double-stranded RNA;

(f) an RNAse III-resistant stem-loop segment from a tRNA inserted at a terminal part of the double-stranded RNA;

(g) at least one GC-rich region at a terminal part of the double-stranded RNA, wherein the at least one GC-rich region includes at least 10 base pairs;

(h) a targetting sequence adjacent to the double-stranded RNA and capable of effecting transport of the double-stranded RNA to a subcellular compartment; and (i) multiple double-stranded RNA stems.

Another aspect of the invention provides a transgenic plant cell (isolated or in differentiated or undifferentiated plant tissue) having in its genome a recombinant DNA construct of this invention. The transgenic plant cell can be an isolated plant cell (e.g., individual plant cells or cells grown in or on an artificial culture medium), or can be a plant cell in undifferentiated tissue (e.g., callus or any aggregation of plant cells). Further provided is a transgenic plant containing the transgenic plant cell of this invention, which can be a plant of any developmental stage, including a regenerated plant, or an inbred or hybrid progeny plant, or seed. Also provided and claimed is a transgenic seed having in its genome a recombinant DNA construct of this invention, and a transgenic plant grown from such seed.

A further aspect of the invention provides a method of providing a transgenic plant having improved resistance to a pest or pathogen of the plant, including: (a) providing a transgenic plant cell having in its genome a recombinant DNA construct of this invention, (b) growing a transgenic plant from the transgenic plant cell, and (c) transcribing the recombinant DNA construct in the transgenic plant, thereby conferring improved resistance to the pest or pathogen in the transgenic plant, relative to a plant in which the recombinant DNA construct is not transcribed.

Yet another aspect of this invention is a composition for imparting to a plant resistance to a pest or pathogen of the plant, including an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. In a preferred embodiment, the plant is provided the composition by transcribing in at least a cell of the plant a recombinant DNA construct of this invention. The composition can further include at least one of: (a) cells of the plant; (b) an insect control agent; and (c) a nematode control agent. Further provided by this invention is a method of imparting to a plant resistance to a pest or pathogen of the plant, including providing to at least one tissue of the plant a composition of this invention.

Other specific embodiments of the invention are disclosed in the following detailed description.

BRIEF DESCRIPTION OF THE DRAWINGS

FIG. 1A is a non-limiting example of a mismatch in the dsRNA resulting from substitution of a single base for one base in the sense strand of the dsRNA. FIG. 1B is a non-limiting example of a mismatch in the dsRNA resulting from substitution of two bases for one base in the sense strand of the dsRNA. FIG. 1C is a non-limiting example of a mismatch in the dsRNA resulting from deletion of a single base in the sense strand of the dsRNA. FIG. 1D is a non-limiting example of a mismatch in the dsRNA resulting from insertion of three or more non-base-paired bases into the sense strand of the dsRNA (SEQ ID NO. 42 for the sense strand). FIG. 1E is a non-limiting example of a mismatch in the dsRNA resulting from insertion of a non-base-paired segment of at least 3 nucleotides in length in both the sense strand and the anti-sense strand of the dsRNA (SEQ ID NO. 43 for the sense strand, and SEQ ID NO. 44 for the anti-sense strand). FIG. 1F is a non-limiting example of an RNAse III-resistant stem-loop segment from a tRNA inserted at a terminal part of the dsRNA.

FIG. 2A, dsRNA encoded by SEQ ID NO. 2; FIG. 2B, dsRNA encoded by SEQ ID NO. 4; FIG. 2C, dsRNA encoded by SEQ ID NO. 5; FIG. 2D, dsRNA encoded by SEQ ID NO. 6; FIG. 2E, dsRNA encoded by SEQ ID NO. 7; FIG. 2F, dsRNA encoded by SEQ ID NO. 8; FIG. 2G, dsRNA encoded by SEQ ID NO. 9; FIG. 2H, dsRNA encoded by SEQ ID NO. 10; FIG. 2I, dsRNA encoded by SEQ ID NO. 11; FIG. 2J, dsRNA encoded by SEQ ID NO. 12; FIG. 2K, dsRNA encoded by SEQ ID NO. 13; and FIG. 2L, dsRNA encoded by SEQ ID NO. 14.

FIG. 4 depicts a non-limiting example of an estimate of $\Delta\Delta G$ values (SEQ ID NO. 1 for the sense strand of the siRNA).

FIG. 6A depicts a non-limiting example of DNA that transcribes to two double-stranded RNA stems. FIG. 6B depicts a representation of the type of multiple double-stranded stem RNA that the DNA of FIG. 6A would be expected to produce (SEQ ID NO. 45 for the polyadenylated tail). FIG. 6C depicts an RNA molecule containing 3 double-stranded stems (SEQ ID NO. 46 for the polyadenylated tail). Abbreviations: "GSE", gene suppression element; "UTR", untranslated region.

FIG. 9A depicts a non-limiting example of a two-stem (H-type) pseudoknot. FIG. 9B depicts a non-limiting example of a three-stem pseudoknot. FIG. 9C depicts a non-limiting example of "kissing stem loops".

DETAILED DESCRIPTION OF THE INVENTION

Figure 1:
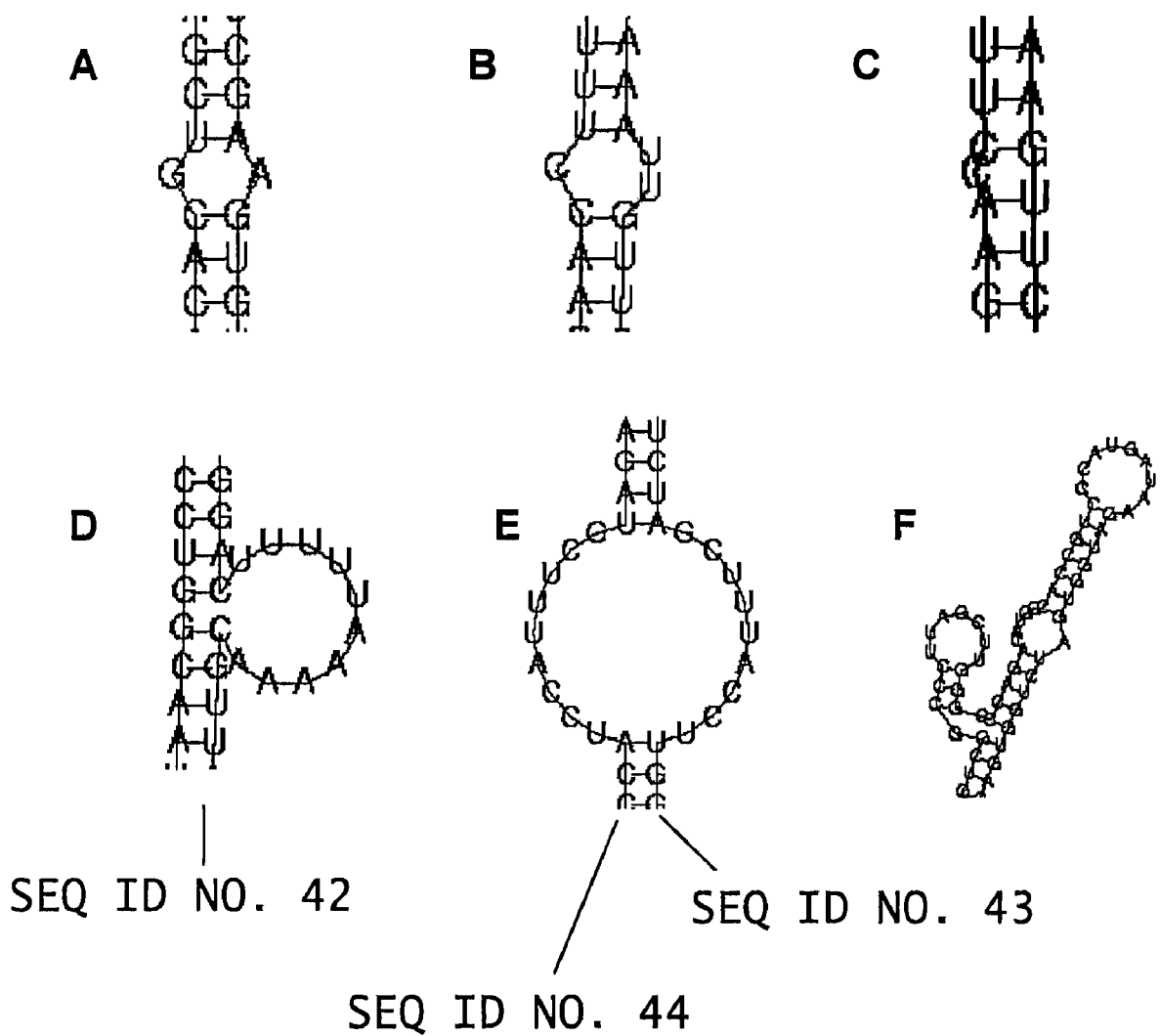
FIG. 1 depicts various embodiments of stabilizing elements as described in detail in the specification.
Figure 2:
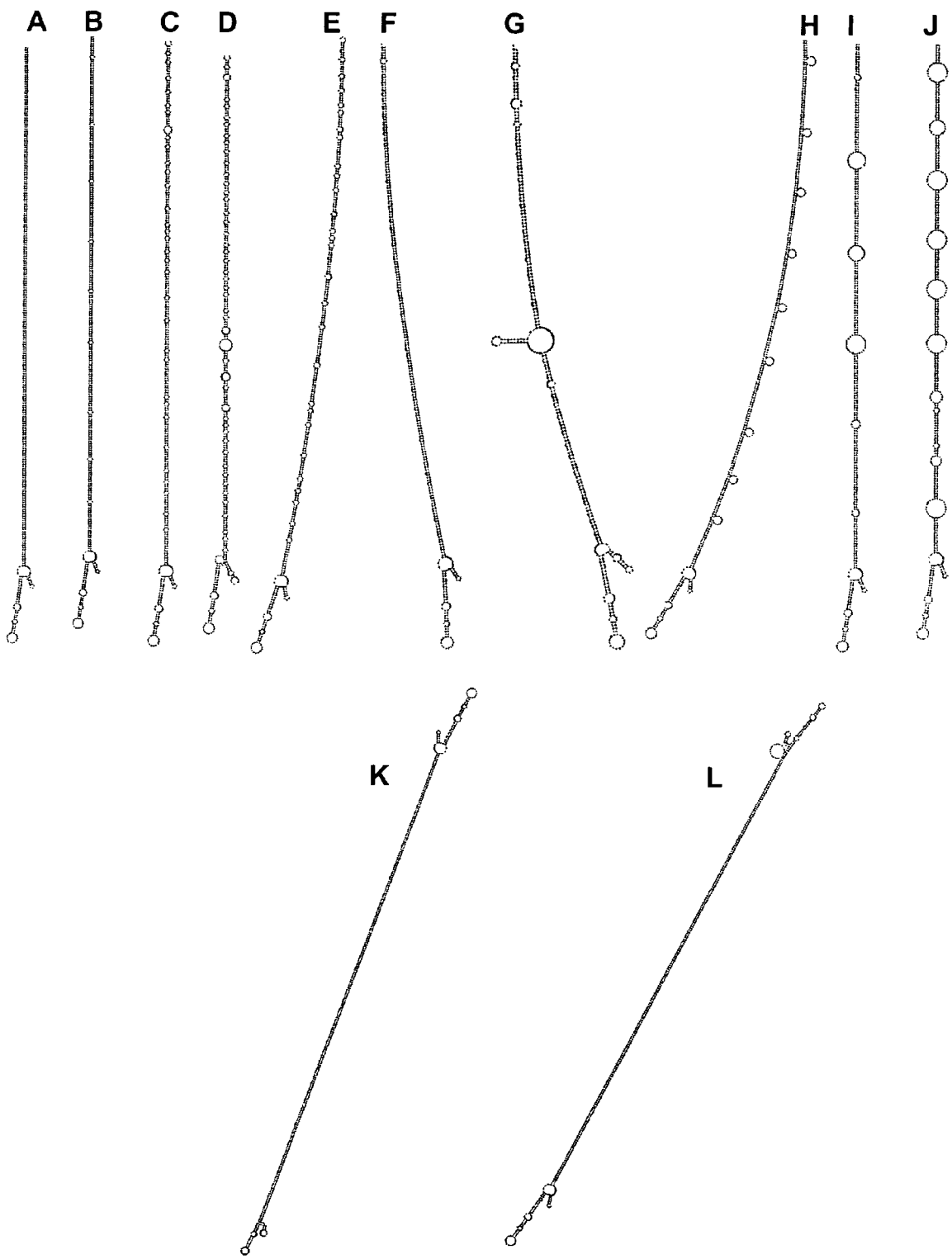
FIG. 2 depicts predicted folded structures of the RNA transcribed from recombinant DNA constructs of this invention as follows.
Figure 3:
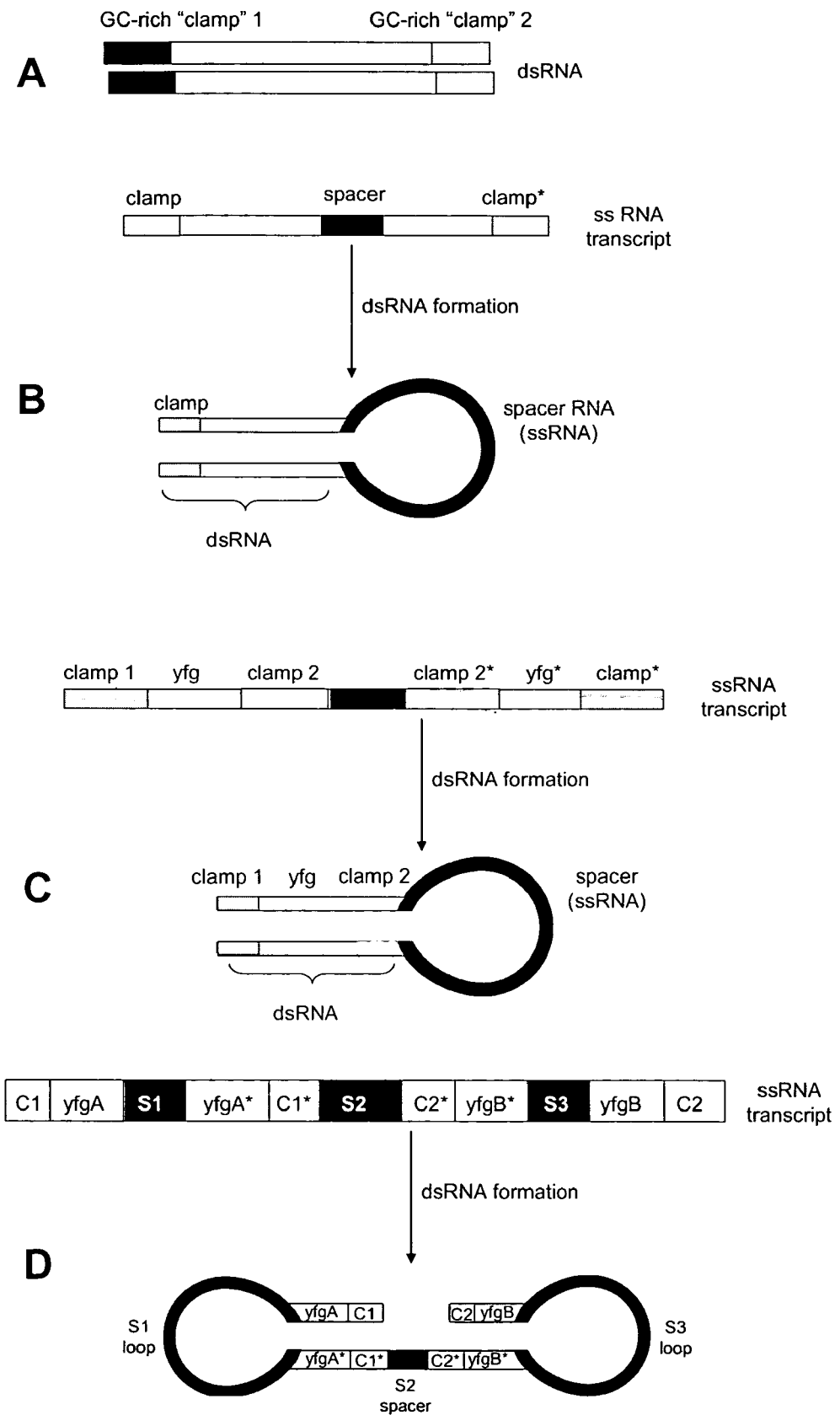
FIG. 3 depicts non-limiting examples of GC-rich regions at the terminal part of a double-stranded RNA, as described in detail in Example 2.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, the inventors also contemplate aspects of the invention described by the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries. The inventors do not intend to be limited to a mechanism or mode of action. Reference thereto is provided for illustrative purposes only.

Recombinant DNA Constructs

This invention provides a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. By "transcribable" is meant that the DNA is capable of being transcribed to RNA. Thus, in preferred embodiments, the recombinant DNA further includes a promoter operably linked to the transcribable DNA.

The RNA for silencing a target gene of a pest or pathogen of a plant is preferably resistant to an RNase III enzyme (for example, Dicer or Dicer-like proteins, including, but not limited to, DCL1, DCL2, DCL3, and DCL4) endogenous to the plant cell in which the recombinant DNA construct is to be transcribed. In a preferred embodiment, the RNA for silencing a target gene of a pest or pathogen of a plant includes double-stranded RNA that remains substantially intact in planta (that is, not reduced in size by the action of an endogenous plant ribonuclease, relative to an RNA lacking the stabilizing feature), but is susceptible to ribonuclease activity once ingested or contacted by the pest or pathogen having the target gene intended to be silenced.

The RNA for silencing a target gene of a pest or pathogen of a plant includes at least about 25 base pairs (bp) of double-stranded RNA (dsRNA). In various embodiments, the dsRNA can include at least about 25, at least about 50, at least about 75, at least about 100, at least about 150, at least about 200, at least about 250, at least about 300, or even more base pairs. In one preferred embodiment, the dsRNA includes at least about 100 base pairs. In another preferred embodiment, the dsRNA includes at least about 250 base pairs. The double-stranded RNA can be in the form of a single double-stranded "stem" (region of base-pairing between sense and anti-sense strands), or can have multiple double-stranded "stems".

When referring to the double-stranded RNA that is transcribed from recombinant DNA constructs of this invention, by "anti-sense" is meant the RNA strand that is intended to base-pair with the mRNA to be silenced, and by "sense" is meant the RNA strand of the double-stranded RNA that is complementary to the anti-sense strand. Base-pairing (complementarity) need not be complete between the sense and anti-sense strands, but is at least sufficient so that under physiological conditions the two strands form double-stranded RNA.

Stabilizing Features

The stabilizing feature of the RNA is one or more selected from the group consisting of:
  (a) a mismatch in the double-stranded RNA resulting from substitution of a single base for one base in the sense strand of the double-stranded RNA;
  (b) a mismatch in the double-stranded RNA resulting from substitution of two bases for one base in the sense strand of the double-stranded RNA;
  (c) a mismatch in the double-stranded RNA resulting from deletion of a single base in the sense strand of the double-stranded RNA;
  (d) a mismatch in the double-stranded RNA resulting from insertion of three or more non-base-paired bases into the sense strand of the double-stranded RNA;
  (e) a mismatch in the double-stranded RNA resulting from insertion of a non-base-paired segment of at least 3 nucleotides in length in both the sense strand and the anti-sense strand of the double-stranded RNA;

(f) an RNAse III-resistant stem-loop segment from a tRNA inserted at a terminal part of the double-stranded RNA;

(g) at least one GC-rich region at a terminal part of the double-stranded RNA, wherein the at least one GC-rich region includes at least 10 base pairs;

(h) a targetting sequence adjacent to the double-stranded RNA and capable of effecting transport of the double-stranded RNA to a subcellular compartment; and (i) multiple double-stranded RNA stems.

In some embodiments, an initial DNA sequence that transcribes to an RNA for silencing a target gene of a pest or pathogen of a plant, wherein the RNA includes double-stranded RNA (dsRNA), is selected for modification, whereby the modifications result in addition of one or more stabilizing features to the RNA. Some of these modifications include C to A, G to T, A to T, and T to A substitutions in the initial DNA sequence. Other modifications include deletion of one or more original bases in the initial DNA sequence. Yet other modifications include insertion of non-base-paired bases in the initial DNA sequence. In various embodiments, the modifications are made in the DNA that transcribes to the sense strand of the dsRNA, in the DNA that transcribes to the anti-sense strand of the dsRNA, in the DNA that transcribes to both the sense and anti-sense strand of the dsRNA, in the DNA that transcribes to single-stranded RNA regions (e.g., in DNA that transcribes to spacer sequence or to single-stranded RNA sequence adjacent to the dsRNA), or in any combination of these. In preferred embodiments, each substitution, deletion, or insertion takes into account its effect on $\Delta\Delta G$ scores. One or more substitution, deletion, or insertion (or combination of these) can be made in the initial DNA sequence to result one or more substitution, deletion, or insertion (or combination of these) in one or more potential siRNA (e.g., a contiguous fragment of 21 base pairs) in the corresponding encoded RNA. These stabilizing features are further described and non-limiting examples illustrated in Example 1. Non-limiting examples of these stabilizing features are depicted in FIGS. 1, 2, 3, 4, and 6.

One embodiment of a stabilizing feature includes a mismatch in the dsRNA resulting from substitution of a single base for one base in the sense strand of the dsRNA (see FIG. 1A). Each such mismatch results in a single-nucleotide bump or bulge on the sense side of the dsRNA.

Another embodiment of a stabilizing feature includes a mismatch in the dsRNA resulting from substitution of two bases for one base in the sense strand of the dsRNA (see FIG. 1B). Each such mismatch results in a larger bulge in the sense side of the dsRNA than that resulting from substitution of a single base for one base in the sense strand.

Another embodiment of a stabilizing feature includes a mismatch in the dsRNA resulting from deletion of a single base in the sense strand of the dsRNA (see FIG. 1C). Each such mismatch results in a single-nucleotide bump or bulge on the anti-sense side of the dsRNA Another embodiment of a stabilizing feature includes a mismatch in the dsRNA resulting from insertion of three or more non-base-paired bases into the sense strand of the dsRNA (see FIG. 1D). In this embodiment, the originally base-paired nucleotides remain, but a segment of non-base-paired nucleotides is inserted into the sense strand of the RNA duplex to form a "loop" protruding from the sense strand. The size of the loop depends on the number of non-base-paired nucleotides that is inserted, which can be 3 or any number greater than 3, including 4, 5, 6, 7, 8, 9, 10, 11, 12, 13, 14, 15, 16, 17, 18, 19, 20, more than about 20, more than about 30, more than about 40, or more than about 50, more than about 60, more than about 70, more than about 80, more than about 90, or even more than about 100 non-base-paired nucleotides.

Another embodiment of a stabilizing feature includes a mismatch in the dsRNA resulting from insertion of a non-base-paired segment of at least 3 nucleotides in length in both the sense strand and the anti-sense strand of the dsRNA (see FIG. 1E). In this embodiment, the originally base-paired nucleotides remain, but additional contiguous pairs (e.g., 3, 4, 5, 6, 7, 8, 9, 10, 11, 12, 13, 14, 15, 16, 17, 18, 19, 20, or even more pairs) of non-complementary nucleotides are inserted. In a preferred embodiment, the insertion is designed to avoid ranges of siRNAs with negative $\Delta\Delta G$ values.

Another embodiment of a stabilizing feature includes an RNAse III-resistant stem-loop segment from a tRNA inserted at a terminal part of the dsRNA (see FIG. 1F). In this embodiment, the recombinant DNA is designed to transcribe to an RNA including at least one RNase III-resistant stem-loop segment from (or derived from) a transfer-RNA (tRNA), added on or near the end of the dsRNA to be stabilized. While a stem-loop structure from a naturally occurring tRNA is a preferred embodiment, variants on the naturally occurring tRNA stem-loop sequences may be used, as well as any other naturally occurring or artificial RNA sequences that include at least one RNase III-resistant tertiary structure (e.g., a stem-loop or one or more dsRNA stems).

Another embodiment of a stabilizing feature includes at least one GC-rich region at a terminal part of the double-stranded RNA, wherein the at least one GC-rich region includes at least 10 base pairs (see FIG. 3). The double-stranded RNA can include two or more GC-rich regions. Each GC-rich region includes opposing strands that are substantially complementary to each other but includes few A and U nucleotides. Thus, the at least one GC-rich region includes multiple GC base pairs; in some embodiments the at least one GC-rich region consists entirely of GC base pairs. In various embodiments, the at least one GC-rich region includes at least 10, at least 20, at least 30, at least 40, at least 50, at least 60, at least 80, at least 100, at least 120, or at least 150 base pairs. The at least one GC-rich region is believed to thermodynamically stabilize the double-stranded RNA because of the stronger base pairing of GC base pairs relative to AU base pairs. Including at least one GC-rich region in the terminal part of a double-stranded RNA preferably increases the double-stranded RNA's ability to silence the target gene (relative to silencing obtained without the at least one GC-rich region). The at least one GC-rich region need not be substantially identical or complementary to the target gene nor need be perfectly double-stranded (i.e., mismatches and gaps are acceptable). In some embodiments, the GC-rich region corresponds to a GC-rich segment of the target gene; in other embodiments, the at least one GC-region includes a synthetic sequence.

Another embodiment of a stabilizing feature includes a targetting sequence adjacent to the double-stranded RNA and capable of effecting transport of the double-stranded RNA to a subcellular compartment. Preferably, the targetting sequence effects transport of the dsRNA to a subcellular compartment that has reduced or no RNase III activity that results in dicing of the dsRNA. Embodiments of such targetting sequences include targetting sequences that direct transport to mitochondria, nucleoli, or plastids (including, but not limited to, chloroplasts, chromoplasts, leucoplasts, and proplastids).

One preferred embodiment includes a targeting sequence that directs transport to mitochondria. For example, many plant mitochondrial tRNAs are transcribed in the nucleus, and then transported to the mitochondria; see, e.g., Delage et al. (2003) *Plant Journal*, 34:623-633. A combination of tRNA anti-codon sequence and overall structure is useful for localization to mitochondria. In one non-limiting example, the dsRNA is stabilized by addition of part or all of the sequences of a mitochondrial tRNA. Plant mitochondrial tRNA sequences are widely available; see, for example, Damiano et al. (2001) *Nucleic Acids Res.*, 29:167-168, which describes the public database PMLItRNA. Other mitochondrial genes are available e.g., the complete mitochondrial genomes have been reported for several higher plants species, including *Arabidopsis thaliana* (Unseld et al. (1997) *Nature Genet.*, 15:57-61), sugar beet, *Beta vulgaris* (Kubo et al. (2000) *Nucleic Acids Res.*, 28: 2571-2576), rapeseed, *Brassica napus* (Handa (2003) *Nucleic Acids Res.*, 31: 5907-5916), maize, *Zea mays* (Clifton et al. (2004) *Plant Physiol.*, 136: 3486-3503), and rice, *Oryza sativa* (Tian et al. (2006) *Plant Physiol.*, 140:401-410).

In another preferred embodiment, the dsRNA is stabilized by addition of a small nucleolar RNA (snRNAs and snoRNAs) targetting sequence; see, for example, Chen et al. (2003) *Nucleic Acids Res.*, 31:2601-2613; Jiang et al. (2002) *Gene*, 294:187-196; Liang et al. (2002) *Nucleic Acids Res.*, 30:3262-3272; and Qi and Ding (2003) *Plant Cell*, 15:2566-2577. One specific embodiment includes a targetting leader sequence such as a 27-nt leader from snRNAs transports the dsRNA to the nucleolus (see, e.g., Paul et al. (2003) *Mol. Therapy*, 7:237-247).

Another preferred embodiment includes a targetting sequence that directs transport to chloroplasts. Chloroplast transformation has been achieved in several plant species, including several important crop species; see, e.g., use of chloroplast targetting sequences from the *Arabidopsis thaliana* 1A Rubisco small subunit gene by Corbin et al. (2001) *Plant Physiol.*, 126:1116-1128, and the extensive discussion in Daniell et al. (2005) *Trends Biotechnol.*, 23:238-45, including lists of promoters and 3' and 5' UTR elements useful in chloroplast transformation in Tables 1 and 2 Ibid. Thus, in some embodiments, the dsRNA is targetted to a plastid, such as a chloroplast, for example, by the use of expression elements (e.g., promoters, transcriptional terminators) such that a dsRNA is formed in the chloroplast. Double-stranded RNAs produced in chloroplasts from transplastmic plants will be stable, yet accessible to plant pests that feed on the plants.

Another embodiment of a stabilizing feature includes multiple double-stranded RNA stems, which imparts improved resistance to a plant RNase III enzyme, relative to an RNA not arranged in the multiple double-stranded RNA stems. In these embodiments, the DNA that transcribes to an RNA for silencing a target gene of a pest or pathogen of a plant can include multiple anti-sense DNA segments that are anti-sense to at least one segment of the target gene and multiple sense DNA segments that are (or are substantially the same as) at least one segment of the target gene, wherein the multiple anti-sense DNA segments and the multiple sense DNA segments are arranged in a series of double-stranded "stems" (FIGS. 5E and 5G), usually connected by loops or spacers of any size or length. Thus, the RNA for silencing a target gene of a pest or pathogen of a plant includes double-stranded RNA which may include dsRNA arranged in a single double-stranded stem or in multiple double-stranded stems.

Figure 5:
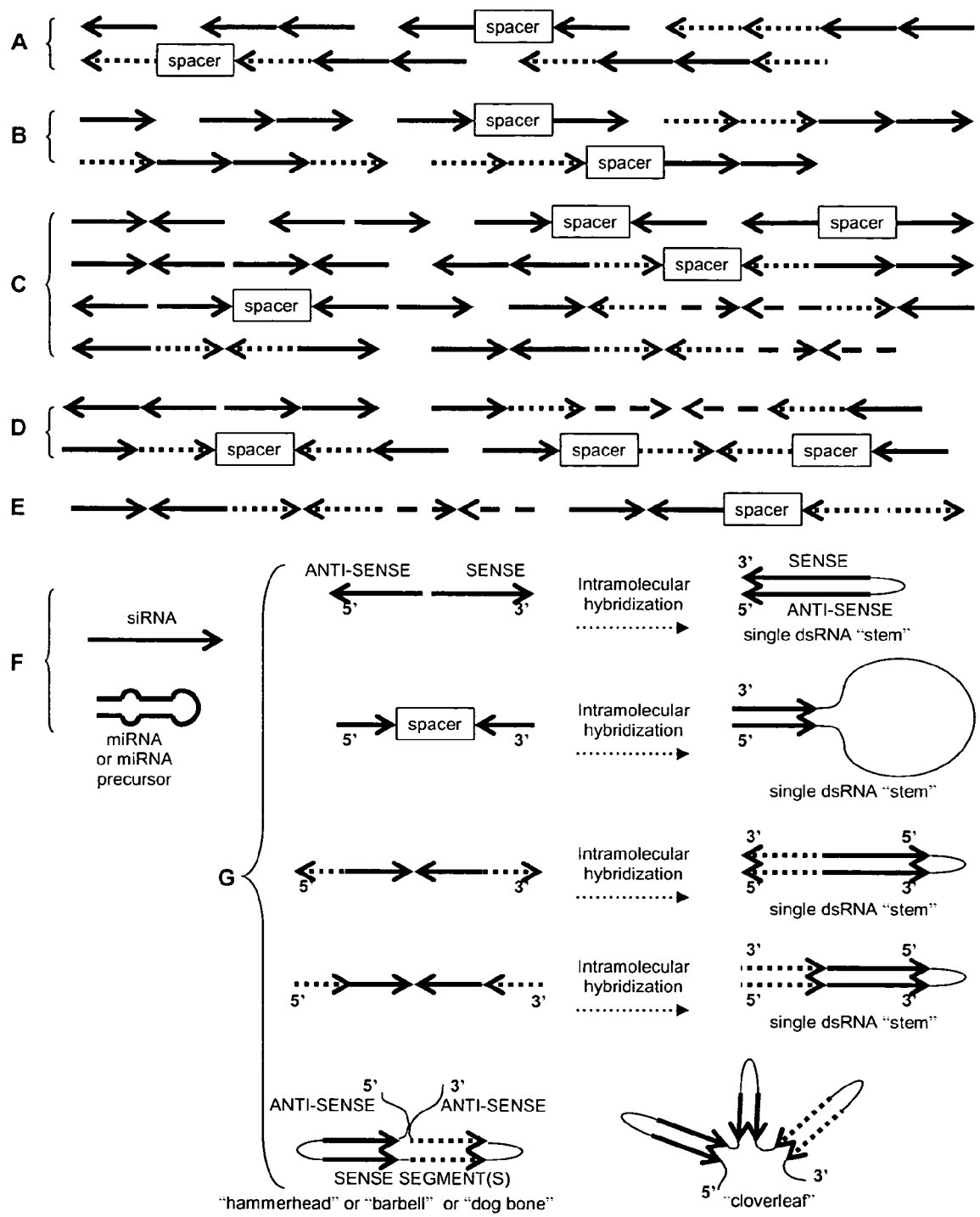
FIG. 5 depicts various non-limiting examples of DNA that transcribes to an RNA for silencing a target gene of a pest or pathogen of a plant useful in the recombinant DNA constructs of the invention. Where drawn as a single strand (FIGS. 5A through 5E), these are conventionally depicted in 5' to 3' (left to right) transcriptional direction, where the arrows indicate anti-sense sequence (arrowhead pointing to the left), or sense sequence (arrowhead pointing to the right). Where drawn as double-stranded (anti-parallel) transcripts (FIG. 5G), the 5' and 3' transcriptional directionality is as shown. Solid lines, dashed lines, and dotted lines indicate sequences that target different target genes (or different segments of a target gene). The DNA that transcribes to an RNA for silencing a target gene of a pest or pathogen of a plant can include: DNA that includes at least one anti-sense DNA segment that is anti-sense to at least one segment of the target gene, or DNA that includes multiple copies of at least one anti-sense DNA segment that is anti-sense to at least one segment of the target gene (FIG. 5A); DNA that includes at least one sense DNA segment that is at least one segment of the target gene, or DNA that includes multiple copies of at least one sense DNA segment that is at least one segment of the target gene (FIG. 5B); DNA that transcribes to RNA for suppressing the target gene by forming double-stranded RNA and includes at least one anti-sense DNA segment that is anti-sense to at least one segment of the target gene and at least one sense DNA segment that is at least one segment of the target gene (FIG. 5C); DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene (FIG. 5D); DNA that transcribes to RNA for suppressing the target gene by forming multiple double-stranded RNA stems and includes multiple anti-sense DNA segments that are anti-sense to at least one segment of the target gene and multiple sense DNA segments that are at least one segment of the target gene, and wherein said multiple anti-sense DNA segments and the multiple sense DNA segments are arranged in a series of inverted repeats (FIG. 5E); DNA that includes nucleotides derived from a microRNA (mRNA) or a mRNA precursor such as a pri-mRNA or pre-mRNA, or DNA that includes nucleotides of a siRNA (FIG. 5F); and DNA that transcribes to RNA for suppressing the target gene by forming single or multiple double stranded RNA stems, with or without spacer sequence.
Figure 6:
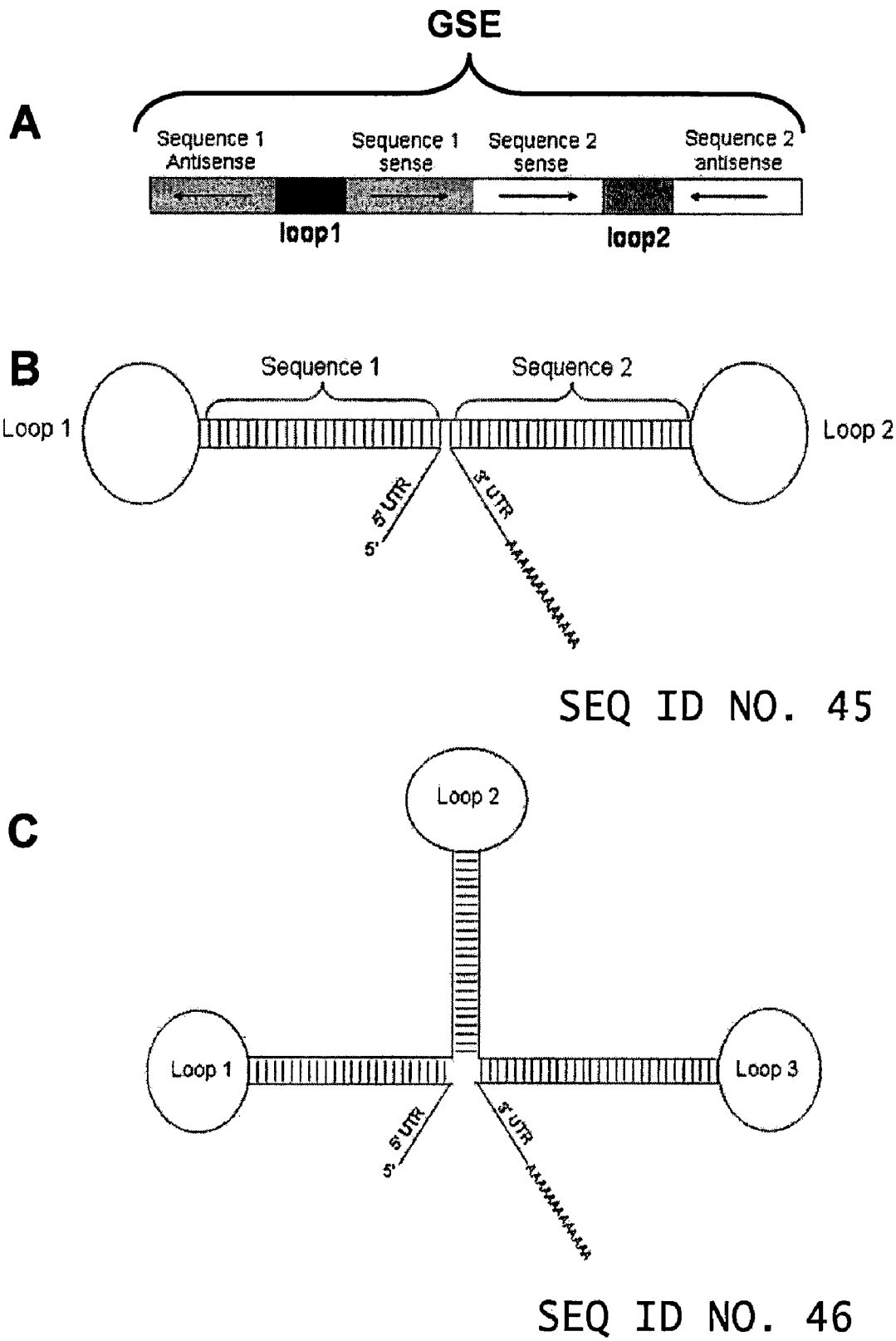
FIG. 6 depicts embodiments of a DNA that transcribes to an RNA for silencing a target gene of a pest or pathogen of a plant, wherein the RNA forms multiple double-stranded stems and has improved resistance to a plant RNase III enzyme, as described in detail in Examples 4 and 5.

In one embodiment, the DNA that transcribes to an RNA for silencing a target gene of a pest or pathogen of a plant forms essentially a single double-stranded RNA and includes multiple serial anti-sense DNA segments that are anti-sense to at least one segment of the target gene and multiple serial sense DNA segments that are at least one segment of the target gene; the multiple serial anti-sense and multiple serial sense segments can form a single double-stranded RNA stem or multiple double-stranded stems in a serial arrangement (with or without non-base paired spacer DNA separating the multiple double-stranded stems). In another embodiment, the DNA that transcribes to an RNA for silencing a target gene of a pest or pathogen of a plant forms multiple dsRNA stems of RNA and includes multiple anti-sense DNA segments that are anti-sense to at least one segment of the target gene and multiple sense DNA segments that are at least one segment of the target gene, and wherein said multiple anti-sense DNA segments and the multiple sense DNA segments are arranged in a series of double-stranded stems. Such multiple double-stranded stems can further be arranged in series or clusters to form tandem or overlapping inverted repeats, which form structures resembling, for example, a two-stem structure resembling a "hammerhead", "barbell", or "dog bone", or a structure containing 3 or more stems resembling a "cloverleaf", or a structure with a pseudoknot-like shape. Any of these constructs can further include spacer DNA segments found within a double-stranded stem (for example, as a spacer between multiple anti-sense or sense DNA segments or as a spacer between a base-pairing anti-sense DNA segment and a sense DNA segment) or outside of a double-stranded stem (for example, as a loop region of sense or of anti-sense or of unrelated RNA sequence, separating a pair of inverted repeats). In cases where base-pairing anti-sense and sense DNA segment are of unequal length, the longer segment can act as a spacer. FIGS. 5 and 6 depict illustrations of possible embodiments of these constructs.

FIG. 5 depicts various non-limiting examples of a DNA that transcribes to an RNA for silencing a target gene of a pest or pathogen of a plant useful in the recombinant DNA constructs of the invention. These include: DNA that transcribes to RNA for silencing the target gene by forming double-stranded RNA and includes at least one anti-sense DNA segment that is anti-sense to at least one segment of the target gene and at least one sense DNA segment that is at least one segment of the target gene (FIG. 5C); DNA that transcribes to RNA for silencing the target gene by forming a single double-stranded RNA and includes multiple serial anti-sense DNA segments that are anti-sense to at least one segment of the at least one first target gene and multiple serial sense DNA segments that are at least one segment of the target gene (FIG. 5D); DNA that transcribes to RNA for silencing the target gene by forming multiple double strands of RNA and includes multiple anti-sense DNA segments that are anti-sense to at least one segment of the target gene and multiple sense DNA segments that are at least one segment of the target gene, and wherein said multiple anti-sense DNA segments and the multiple sense DNA segments are arranged in a series of inverted repeats (FIG. 5E); and DNA that includes nucleotides derived from a mRNA, or DNA that includes nucleotides of a siRNA (FIG. 5F).

FIG. 5G depicts various non-limiting arrangements of double-stranded RNA (dsRNA) that can be transcribed from embodiments of the recombinant DNA constructs of the invention. When such dsRNA is formed, it can silence one or more target genes, and can form a single double-stranded stem or multiple double-stranded stems. Where multiple double-stranded "stems" are formed, they can be arranged in any way, for example, in a "hammerhead" or "barbell" or "dog bone" arrangement, or in a "cloverleaf" arrangement. In some embodiments, the double-stranded stems can form a "pseudoknot" arrangement (e.g., where spacer or loop RNA of one double-stranded stem forms part of a second double-stranded stem); see, for example, Staple and Butcher (2005) *PLoS Biol.*, 3(6):e213. Spacer DNA (located between or adjacent to dsRNA regions) is optional but commonly included and generally includes DNA that does not correspond to the target gene (although in some embodiments can include sense or anti-sense DNA of the target gene). Spacer DNA can include sequence that transcribes to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity.

FIG. 6A depicts a non-limiting DNA (gene suppression element or "GSE") that transcribes to an RNA for silencing a target gene of a pest or pathogen of a plant useful in recombinant DNA constructs of the invention, as described in Example 5. The transcribed RNA includes multiple double-stranded stems that impart improved resistance to a plant RNase III enzyme relative to an RNA lacking the multiple dsRNA stems. FIG. 6B depicts a representation of the type of multiple double-stranded stems that the GSE of FIG. 6A would be expected to produce. In this non-limiting example, orientations of the sequences are anti-sense followed by sense for sequence 1, then sense followed by anti-sense for sequence 2 (FIG. 6A). Analogous recombinant DNA constructs could be designed to provide RNA molecules containing more than 2 double-stranded stems, as shown in FIG. 6C, which depicts an RNA molecule containing 3 double-stranded stems.

In RNA-mediated post-transcriptional gene silencing, dsRNA is processed by RNase III enzymes Dicer (or by Dicer-like proteins) into small double-stranded RNAs known as short interfering RNAs (siRNAs), which typically range in size from about 20 to about 25 base pairs (in plants, commonly 21 base pairs or 24 base pairs). After double stranded siRNAs are generated, one RNA strand is incorporated into the RNA-induced silencing complex (RISC). Typically, an siRNA double-stranded duplex is functionally asymmetric in terms of which strand (sense or anti-sense) is incorporated into RISC, a requirement for silencing. The difference in free energy (the "$\Delta\Delta G$" score) of the two strands of an siRNA is an indication of the difference in stability between the two ends of an siRNA. Approximately 80% of functional siRNAs that have been reported in the literature have a negative $\Delta\Delta G$ for the strand that is incorporated into RISC; in other words, the strand whose 5' end is less tightly base-paired is more likely to be incorporated into RISC. Thus the $\Delta\Delta G$ score predicts which strand of an siRNA (sense or anti-sense) is most likely to be incorporated into RISC.

Some of the embodiments of the stabilizing features include imperfect dsRNA duplexes. In preferred embodiments, the dsRNA is additionally designed to increase bias for the anti-sense strand (rather than the sense strand) to be preferentially incorporated into the RISC complex. In recombinant DNA constructs of this invention, where the stabilizing feature is an introduced imperfection in the dsRNA, the nucleotide changes that create the imperfection are preferably selected based on $\Delta\Delta G$ scores, in order to favor incorporation of the anti-sense strand into the RISC complex.

One non-limiting technique for calculating a $\Delta\Delta G$ score of an siRNA is by using the values in Khvorova et al. (2003) *Cell*, 115, 209-216, provided here in Table 1, in the equation: $\Delta\Delta G$=–(sum of minimal free energy of first 4 residues of 5' sense strand) minus–(sum of minimal free energy of first 4 residues of 5' anti-sense strand). These values are empirical and take into consideration the nearest neighbour effect of a nucleotide directly adjacent to a given base pair.

TABLE 1

Free Energy Values for Calculating Internal Stability of RNA Duplexes (–kcal/mol)*

| First Nucleotide | Second Nucleotide | | | |
|---|---|---|---|---|
| Base Pair | A | C | G | U |
| A-U | 1.1 | 2.4 | 1.9 | 1.1 |
| C-G | 2.2 | 3.3 | 2.2 | 1.9 |
| G-C | 2.7 | 3.8 | 3.3 | 2.4 |
| G-U | 1.5 | 2.7 | 2.2 | 1.4 |
| U-A | 1.4 | 2.6 | 2.2 | 1.1 |

*from Khvorova et al. (2003) Cell, 115, 209-216

The more positive a $\Delta\Delta G$ is for a given siRNA, the more likely it is that the sense strand of that siRNA will be incorporated into RISC. Introducing an imperfection (such as a mismatch) into a dsRNA intended for processing and incorporation into RISC is preferably accomplished with consideration of $\Delta\Delta G$ values so as to increase the likelihood of the anti-sense strand to be incorporated into RISC. The more positive a $\Delta\Delta G$ is for a given siRNA, the larger the minimal free energy changes must be in order to bias RISC incorporation toward the anti-sense strand. Conversely, an siRNA with a negative $\Delta\Delta G$ (especially a strongly negative $\Delta\Delta G$) may tolerate an increase in $\Delta\Delta G$ and still have the anti-sense strand preferred by RISC. Introduction of a stabilizing feature can negatively impact adjacent potential siRNAs; e.g., a mismatch in an end of one set of potential siRNAs may negatively affect potential siRNAs within about 19 nucleotides offset from the introduced mismatch. Thus, in preferred embodiments, the introduction of stabilizing features (such as a mismatch) is carried out such that the resulting overall population of anti-sense siRNAs is more likely to be incorporated into RISC.

FIG. 4 depicts a non-limiting example illustrating the $\Delta\Delta G$ estimate, wherein the 5' end of the sense strand and the 5' end of the corresponding anti-sense strand of a given siRNA were compared. The siRNA is shown with the sense strand having the sequence GATCTAGCCGAAATTGTGC (SEQ ID NO. 1) (written 5' to 3' in the left to right direction); the four 5'-most bases of the corresponding anti-sense strand (written 5' to 3' in the right to left direction) are depicted above the sense strand. Free energy values were calculated for the four 5'-most bases of each strand. To do this, the 5'-most base pair and the nucleotide immediately proximal and 3' to that base pair on the strand for which the free energy value is being calculated were identified, and the values for that combination were found in Table 1. This was repeated for the next three proximal base pair/adjacent nucleotide arrangements. Thus, in the example given in FIG. 4, for the anti-sense strand, the four base pair/adjacent nucleotide arrangements under consideration (with their respective free energy values given in parentheses) were G-C and C (3.8), C-G and A (2.2), A-T and C (2.4), and C-G and A (2.2); the (negative) sum of these free energies resulted in a $\Delta G$ of –10.6 for the anti-sense strand. Similarly, in the example shown in FIG. 4, for the sense strand, the four base pair/adjacent nucleotide arrangements under consideration (with their respective free energy values given in parentheses) were G-C and A (2.7), A-T and T (1.1), T-A and C (2.6), and C-G and T (1.9); the (negative) sum of these free energies resulted in a $\Delta G$ of –8.3 for the sense strand. Thus, in this example, the sense strand was predicted to be preferably incorporated into RISC. Note that the free energy value for a given base pair (e.g., G-C, which in the example depicted in FIG. 4 is the 5'-most base pair in both the anti-sense strand and in the sense strand) can be strongly influenced by its nearest neighbor (in this example, 3.8 for the G-C pair in the anti-sense strand and 2.7 for the G-C pair in the sense strand).

Target Genes of Pests or Pathogens

One aspect of the invention provides recombinant DNA constructs wherein the target gene is exogenous to the plant in which the construct is to be transcribed, but endogenous to a pest or pathogen (e.g., viruses, bacteria, fungi, and invertebrates such as insects, nematodes, and molluscs) of the plant. The target gene can include multiple target genes, or multiple segments of one or more genes. In one preferred embodiment, the target gene or genes is a gene or genes of an invertebrate pest or pathogen of the plant. These recombinant DNA constructs are particularly useful in providing transgenic plants having resistance to one or more plant pests or pathogens, for example, resistance to a nematode such as soybean cyst nematode or root knot nematode or to a pest insect.

The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, RNA components of ribosomes or ribozymes, small nucleolar RNAs, and other non-coding RNAs (see, for example, Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124). One specific example of a target gene includes a microRNA recognition site (that is, the site on an RNA strand to which a mature miRNA binds and induces cleavage). Another specific example of a target gene includes a microRNA precursor sequence native to a pest or pathogen of the transgenic plant, that is, the primary transcript encoding a microRNA, or the RNA intermediates processed from this primary transcript (e.g., a nuclear-limited pri-miRNA or a pre-miRNA which can be exported from the nucleus into the cytoplasm). See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr Genomics*, 5:129-135. Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

In many preferred embodiments, the target gene is an essential gene of the plant pest or pathogen. Essential genes include genes that are required for development of the pest or pathogen to a fertile reproductive adult. Essential genes include genes that, when silenced or suppressed, result in the death of the organism (as an adult or at any developmental stage, including gametes) or in the organism's inability to successfully reproduce (e.g., sterility in a male or female parent or lethality to the zygote, embryo, or larva). A description of nematode essential genes is found, e. g., in Kemphues K. "Essential Genes" (Dec. 24, 2005), WormBook, ed. The *C. elegans* Research Community, WormBook, doi/10.1895/ wormbook.1.57.1. Non-limiting examples of nematode essential genes include major sperm protein, RNA polymerase II, and chitin synthase (see, e.g., U. S. Patent Application Publication US20040098761 A1); additional soybean cyst nematode essential genes are provided in U.S. patent application Ser. No. 11/360,355, filed 23 Feb. 2006, incorporated by reference herein. A description of insect genes is publicly available at the *Drosophila* genome database (FlyBase). The majority of predicted *Drosophila* genes have been analyzed for function by a cell culture-based RNA interference screen, resulting in 438 essential genes being identified; see Boutros et al. (2004) *Science*, 303:832-835. A description of bacterial and fungal essential genes is provided in the Database of Essential Genes ("DEG"); see Zhang et al. (2004) *Nucleic Acids Res.*, 32:D271-D272.

Plant pest invertebrates include, but are not limited to, pest nematodes, pest molluscs (slugs and snails), and pest insects. Plant pathogens of interest include fungi, bacteria (e. g., the bacteria that cause leaf spotting, fireblight, crown gall, and bacterial wilt), mollicutes, and viruses (e. g., the viruses that cause mosaics, vein banding, flecking, spotting, or abnormal growth). See also G. N. Agrios, "Plant Pathology" (Fourth Edition), Academic Press, San Diego, 1997, 635 pp., for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005.

Non-limiting examples of fungal plant pathogens of particular interest include, e.g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., *Alternaria* spp., and *Phytophthora* spp. Specific examples of fungal plant pathogens include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani*, *Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis*, *Sporisorium holci-sorghi*, *Colletotrichum graminicola*, *Setosphaeria turcica*, *Aureobasidium zeae*, *Phytophthora infestans*, *Phytophthora sojae*, *Scierotinia sclerotiorum*, and the numerous fungal species provided in Tables 4 and 5 of U.S. Pat. No. 6,194,636, which is incorporated in its entirety by reference herein.

Non-limiting examples of bacterial pathogens include the mycoplasmas that cause yellows disease and *spiroplasmas* such as *Spiroplasma kunkelii*, which causes corn stunt, eubacteria such as *Pseudomonas avenae*, *Pseudomonas andropogonis*, *Erwinia stewartii*, *Pseudomonas syringae* pv. *syringae*, *Xylella fastidiosa*, and the numerous bacterial species listed in Table 3 of U.S. Pat. No. 6,194,636, which is incorporated in its entirety by reference herein.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636, which is incorporated in its entirety by reference herein.

Non-limiting examples of invertebrate pests include cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as phylloxera (*Daktulosphaira vitifoliae*), corn borers, cutworms, armyworms, leafhoppers, Japanese beetles, grasshoppers, and other pest coleopterans, dipterans, and lepidopterans. Specific examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), clay-backed cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is incorporated in its entirety by reference herein.

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, mRNAs, mRNA precursor molecules, mRNA promoters, as well as other genes such as those disclosed in United States Patent Application Publication 2006/0021087 A1, PCT Patent Application PCT/JUS05/11816, and in Table II of United States Patent Application Publication 2004/0098761 A1, which are incorporated by reference herein. Target genes from pathogens can include genes for viral translation initiation factors, viral replicases, mRNAs, mRNA precursor molecules, fungal tubulin, fungal vacuolar ATPase, fungal chitin synthase, fungal MAP kinases, fungal PacI Tyr/Thr phosphatase, enzymes involved in nutrient transport (e.g., amino acid transporters or sugar transporters), enzymes involved in fungal cell wall biosynthesis, cutinases, melanin biosynthetic enzymes, polygalacturonases, pectinases, pectin lyases, cellulases, proteases, genes that interact with plant avirulence genes, and other genes involved in invasion and replication of the pathogen in the infected plant.

The recombinant DNA constructs of the invention can be designed to be more specifically suppress a target gene of a pest or pathogen of a plant, by designing the RNA for silencing the target gene to include regions substantially non-identical to a non-target gene sequence. Non-target genes can include any gene not intended to be silenced or suppressed, either in a plant transcribing the recombinant DNA construct or in non-target organisms that may come into contact with RNA transcribed from the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a specific pest or pathogen of a plant, and the non-target gene can be, e.g., a gene of a non-target species, such as a plant or a gene of a virus, fungus, bacterium, invertebrate, or vertebrate, even a human. One non-limiting example is where the RNA for silencing the target gene is designed to suppress a target gene that is a gene endogenous to a single species (e.g., Western corn rootworm, *Diabrotica virgifera virgifera* LeConte) but to not suppress a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the RNA for silencing the target gene to suppress a target gene sequence common to the multiple species in which the target gene is to be silenced. Thus, an RNA for silencing the target gene can be selected to be specific for one taxon (for example, specific to a genus, family, or even a larger taxon such as a phylum, e.g., arthropoda) but not for other taxa (e.g., plants or vertebrates or mammals). In one non-limiting example of this embodiment, an RNA for silencing a target gene can be selected so as to target pathogenic fungi (e.g., a *Fusarium* spp.) but not target any gene sequence from beneficial fungi.

In another non-limiting example of this embodiment, an RNA for silencing a target gene in corn rootworm can be selected to be specific to all members of the genus *Diabrotica*. In a further example of this embodiment, such a *Diabrotica*-targetted RNA can be selected so as to not target any gene sequence from beneficial coleopterans (for example, predatory coccinellid beetles, commonly known as ladybugs or ladybirds) or other beneficial insect species including beneficial pollinators.

The required degree of specificity of an RNA for silencing a target gene depends on various factors. For example, the RNA for silencing a target gene includes double-stranded RNA (dsRNA), and thus factors can include the size of the smaller dsRNA fragments that are expected to be produced by the action of Dicer or dicer-like proteins, and the relative importance of decreasing the dsRNA's potential to suppress non-target genes. For example, where the dsRNA fragments are expected to be 21 base pairs in size, one particularly preferred embodiment includes RNA for silencing a target gene that encodes regions substantially non-identical to a non-target gene sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target gene sequence. In another embodiment, regions substantially non-identical to a non-target gene sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target gene sequence.

In some embodiments, it may be desirable to design the RNA for silencing a target gene to include regions predicted to not generate undesirable polypeptides, for example, by screening the RNA for silencing a target gene for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database or the Biotechnology Information for Food Safety Databases (see, for example, Gendel (1998) *Adv. Food Nutr. Res.*, 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system of National Center for Biotechnology Information, National Institute of Health website . Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish. Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles.

In one non-limiting example, an RNA for silencing a target gene is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in an RNA for silencing a target gene.

Since the RNA for silencing a target gene includes double-stranded RNA (dsRNA), applicants recognize that in some dsRNA-mediated gene silencing, it is possible for imperfectly matching dsRNA sequences to be effective at gene silencing. For example, it has been shown that mismatches near the center of a mRNA complementary site has stronger effects on the mRNA's gene silencing than do more distally located mismatches. See, for example, FIG. 4 in Mallory et al. (2004) *EMBO J.*, 23:3356-3364. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.*, 33:1671-1677). Thus, the dsRNA that is included in the RNA for silencing a target gene need not always have 100% sequence identity with the intended target gene, but generally would preferably have substantial sequence identity with the intended target gene, such as about 95%, about 90%, about 85%, or about 80% sequence identity with the intended target gene. One skilled in the art would be capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, it may be desirable for an RNA for silencing a target gene to be active across several species, and therefore one skilled in the art can determine that it is more important to include in the RNA for silencing a target gene regions specific to the several species of interest, but less important to screen for regions predicted to have higher gene silencing efficiency or for regions predicted to generate undesirable polypeptides.

Various embodiments of the recombinant DNA construct of this invention include, in addition to the transcribable DNA, one or more of the following elements:

(a) a plant promoter (b) a ribozyme flanking the transcribable DNA;

(c) an intron, in which the transcribable DNA is embedded;

(d) DNA that transcribes to an RNA aptamer capable of binding to a ligand;

(e) DNA that transcribes to an RNA aptamer capable of binding to a ligand and DNA that transcribes to regulatory RNA capable of regulating expression of a target sequence, wherein the regulation is dependent on the conformation of the regulatory RNA, and the conformation of the regulatory RNA is allosterically affected by the binding state of the RNA aptamer;

(f) at least one gene expression element; and (g) at least one T-DNA border.

These elements are described in more detail below.

Promoters

Generally, the recombinant DNA construct of this invention includes a plant promoter operably linked to the transcribable DNA. In various embodiments, the promoter is selected from the group consisting of a constitutive promoter, a spatially specific promoter, a temporally specific promoter, a developmentally specific promoter, and an inducible promoter.

Non-constitutive promoters suitable for use with the recombinant DNA constructs of the invention include spatially specific promoters, temporally specific promoters, and inducible promoters. Spatially specific promoters can include organelle-, cell-, tissue-, or organ-specific promoters (e.g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e.g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters".

Promoters of particular interest include the following non-limiting examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837,848; 6,437,217 and 6,426,446; a maize L3 oleosin promoter disclosed in U.S. Pat. No. 6,433,252; a promoter for a plant nuclear gene encoding a plastid-localized aldolase disclosed in U. S. Patent Application Publication 2004/0216189; cold-inducible promoters disclosed in U.S. Pat. No. 6,084,089; salt-inducible promoters disclosed in U.S. Pat. No. 6,140,078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/0123347 A1. All of the above-described patents and publications disclosing promoters and their use, especially in recombinant DNA constructs functional in plants are incorporated herein by reference.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol. Cell Biol.*, 5:451-463, Davidson and Ellington (2005) *Trends Biotechnol.*, 23:109-112, Winkler et al. (2002) *Nature*, 419:952-956, Sudarsan et al. (2003) *RNA*, 9:644-647, and Mandal and Breaker (2004) *Nature Struct. Mol. Biol.*, 11:29-35. Such "riboregulators" could be selected or designed for specific spatial or temporal specificity, for example, to regulate translation of the exogenous gene only in the presence (or absence) of a given concentration of the appropriate ligand.

Ribozymes

Ribozymes of use in the invention include naturally occurring and synthetic ribozymes including, but not limited to, self-splicing group I introns, hairpin ribozymes, cis-acting and trans-acting hammerhead ribozymes. Also useful in the invention are the natural or engineered sequences including the functional catalytic domains from ribozymes (see, for example, Ohuchi et al. (2004) *Nucleic Acids Res.*, 30: 3473-3480).

Introns

As used herein, "intron" or "intron sequence" generally means non-coding DNA sequence from a natural gene, which retains in the recombinant DNA constructs of this invention its native capability to be excised from pre-mRNA transcripts, e.g., native intron sequences found with associated protein coding RNA regions, wherein the native introns are spliced, allowing exons to be assembled into mature mRNAs before the RNA leaves the nucleus. Introns can be self-splicing or non-self-splicing (that is, requiring enzymes or a spliceosome for splicing to occur) and can be selected for different splicing efficiency. Essentially any intron can be used in recombinant DNA constructs of this invention as a host for embedding the transcribable DNA. The intron is generally found adjacent (with or without some intervening sequence), and operably linked to, the promoter. In some embodiments, the intron is also adjacent (with or without some intervening sequence) to a terminator. In one preferred embodiment, the intron containing the transcribable DNA is flanked directly (on the 5' end) by the promoter, and (on the 3' end) by the terminator if present.

Introns suitable for use in constructs of the invention can be viral introns (e.g., Yamada et al. (1994) *Nucleic Acids Res.*, 22:2532-2537), eukaryotic introns (including animal, fungal, and plant introns), archeal or bacterial introns (e.g., Belfort et al. (1995) *J. Bacteriol.*, 177:3897-3903), or any naturally occurring or artificial (e.g., Yoshimatsu and Nagawa (1989) *Science*, 244:1346-1348) DNA sequences with intron-like functionality in the plant in which the recombinant DNA construct of the invention is to be transcribed. Where a recombinant DNA construct of the invention is used to transform a plant, plant-sourced introns can be especially preferred. While essentially any intron can be used in the practice of this invention as a host for embedded DNA, particularly preferred are introns that are introns that enhance expression in a plant or introns that are derived from a 5' untranslated leader sequence. Examples of especially preferred plant introns include a rice actin 1 intron (I-Os-Act1) (Wang et al. (1992) *Mol. Cell Biol.*, 12:3399-3406; McElroy et al. (1990) *Plant Cell*, 2:163-171), a maize heat shock protein intron I-Zm-hsp70) (U.S. Pat. Nos. 5,593,874 and 5,859,347), and a maize alcohol dehydrogenase intron (I-Zm-adh1) (Callis et al. (1987) *Genes Dev.*, 1:1183-1200). Other examples of introns suitable for use in the invention include the tobacco mosaic virus 5' leader sequence or "omega" leader (Gallie and Walbot (1992) *Nucleic Acids Res.*, 20:4631-4638), the Shrunken-1 (Sh-1) intron (Vasil et al. (1989) *Plant Physiol.*, 91:1575-1579), the maize sucrose synthase intron (Clancy and Hannah (2002) *Plant Physiol.*, 130:918-929), the heat shock protein 18 (hsp18) intron (Silva et al. (1987) *J. Cell Biol.*, 105:245), and the 82 kilodalton heat shock protein (hsp82) intron (Semrau et al. (1989) *J. Cell Biol.*, 109, p. 39A, and Mettler et al. (May 1990) N.A.T.O. Advanced Studies Institute on Molecular Biology, Elmer, Bavaria).

Aptamers

Nucleic acid aptamers are nucleic acid molecules that bind to a ligand through binding mechanism that is not primarily based on Watson-Crick base-pairing (in contrast, for example, to the base-pairing that occurs between complementary, anti-parallel nucleic acid strands to form a double-stranded nucleic acid structure). See, for example, Ellington and Szostak (1990) *Nature*, 346:818-822. A nucleic acid aptamer generally includes a primary nucleotide sequence that allows the aptamer to form a secondary structure (e.g., by forming stem-loop structures) that allows the aptamer to bind to its ligand. Binding of the aptamer to its ligand is preferably specific, allowing the aptamer to distinguish between two or more molecules that are structurally similar (see, for example, Bayer and Smolke (2005) *Nature Biotechnol.*, 23:337-343). Aptamers useful in the invention can, however, be monovalent (binding a single ligand) or multivalent (binding more than one individual ligand, e.g., binding one unit of two or more different ligands). See, for example, Di Giusto and King (2004) *J. Biol. Chem.*, 279:46483-46489, describing the design and construction of multivalent, circular DNA aptamers.

Aptamers useful in the invention can include DNA, RNA, nucleic acid analogues (e.g., peptide nucleic acids), locked nucleic acids, chemically modified nucleic acids, or combinations thereof. See, for example, Schmidt et al. (2004) *Nucleic Acids Res.*, 32:5757-5765, who describe locked nucleic acid aptamers. In one preferred embodiment of the invention, the aptamer is an RNA aptamer. In a particularly preferred embodiment, the aptamer is produced by transcription in planta. Examples of aptamers can be found, for example, in the public Aptamer Database, available on line at aptamer.icmb.utexas.edu (Lee et al. (2004) *Nucleic Acids Res.,* 32(1):D95-100).

Aptamers can be designed for a given ligand by various procedures known in the art, including in vitro selection or directed evolution techniques. See, for example, "SELEX" ("systematic evolution of ligands by exponential enrichment"), as described in Tuerk and Gold (1990) *Science,* 249: 505-510, Ellington and Szostak (1990) *Nature,* 346:818-822, Ellington and Szostak (1992) *Nature,* 355:850-852, selection of bifunctional RNA aptamers by chimeric SELEX, as described by Burke and Willis (1998), *RNA,* 4:1165-1175, selection using ligands bound to magnetic particles as described by Murphy et al. (2003) *Nucleic Acids Res.,* 31:e110, an automated SELEX technique described by Eulberg et al. (2005) *Nucleic Acids Res.,* 33(4):e45, and a SELEX-type technique for obtaining aptamers raised against recombinant molecules expressed on cell surfaces, as descried by Ohuchi et al. (2005) *Nucleic Acid Symposium Series,* 49:351-352 Selection can begin with a random pool of RNAs, from a partially structured pool of RNAs (see, for example, Davis and Szostak (2002) *Proc. Natl. Acad. Sci. USA,* 99: 11616-11621), or from a pool of degenerate RNAs (see, for example, Geiger et al. (1996) *Nucleic Acids Res.,* 24: 1029-1036). Secondary structure models, folding, and hybridization behavior for a given RNA sequence can be predicted using algorithms, e.g., as described by Zuker (2003) *Nucleic Acids Res.,* 31: 3406-3415. Thus, aptamers for a given ligand can be designed de novo using suitable selection. One non-limiting example of aptamer design and selection is described in detail in Weill et al. (2004) *Nucleic Acids Res.,* 32:5045-5058, which describes isolation of various ATP-binding aptamers and secondary selection of aptamers that bind cordycepin (3' deoxyadenosine). Another non-limiting example of aptamer design is given in Huang and Szostak (2003) *RNA,* 9:1456-1463, which describes the in vitro evolution of novel aptamers with new specificities and new secondary structures from a starting aptamer.

Ligands useful in the invention can include amino acids or their biosynthetic or catabolic intermediates, peptides, proteins, glycoproteins, lipoproteins, carbohydrates, fatty acids and other lipids, steroids, terpenoids, hormones, nucleic acids, aromatics, alkaloids, natural products or synthetic compounds (e.g., dyes, pharmaceuticals, antibiotics, herbicides), inorganic ions, and metals, in short, any molecule (or part of a molecule) that can be recognized and be bound by a nucleic acid secondary structure by a mechanism not primarily based on Watson-Crick base pairing. In this way, the recognition and binding of ligand and aptamer is analogous to that of antigen and antibody, or of biological effector and receptor. Ligands can include single molecules (or part of a molecule), or a combination of two or more molecules (or parts of a molecule), and can include one or more macromolecular complexes (e.g., polymers, lipid bilayers, liposomes, cellular membranes or other cellular structures, or cell surfaces). See, for example, Plummer et al. (2005) *Nucleic Acids Res.,* 33:5602-5610, which describes selection of aptamers that bind to a composite small molecule-protein surface; Zhuang et al. (2002) *J. Biol. Chem.,* 277:13863-13872, which describes the association of insect mid-gut receptor proteins with lipid rafts, which affects the binding of *Bacillus thuringiensis* insecticidal endotoxins; and Homann and Goringer (1999) *Nucleic Acids Res.,* 27:2006-2014, which describes aptamers that bind to live trypanosomes.

Non-limiting examples of specific ligands include vitamins such as coenzyme $B_{12}$ and thiamine pyrophosphate, flavin mononucleotide, guanine, adenosine, S-adenosylmethionine, S-adenosylhomocysteine, coenzyme A, lysine, tyrosine, dopamine, glucosamine-6-phosphate, caffeine, theophylline, antibiotics such as chloramphenicol and neomycin, herbicides such as glyphosate, glufosinate, sulfonylureas, imidazolinones, bromoxynil, dalapon, dicamba, cyclohezanedione, protoporphyrinogen oxidase inhibitors, and isoxaflutole herbicides, proteins including viral or phage coat proteins and invertebrate epidermal or digestive tract surface proteins, and RNAs including viral RNA, transfer-RNAs (t-RNAs), ribosomal RNA (rRNA), and RNA polymerases such as RNA-dependent RNA polymerase (RdRP). One class of RNA aptamers useful in the invention are "thermoswitches" that do not bind a ligand but are thermally responsive, that is to say, the aptamer's conformation is determined by temperature. See, for example, Box 3 in Mandal and Breaker (2004) *Nature Rev. Mol. Cell Biol.,* 5:451-463.

An aptamer can be described by its binding state, that is, whether the aptamer is bound (or unbound) to its respective ligand. The binding site (or three-dimensional binding domain or domains) of an aptamer can be described as occupied or unoccupied by the ligand. Similarly, a population of a given aptamer can be described by the fraction of the population that is bound or unbound to the ligand. The affinity of an aptamer for its ligand can be described in terms of the rate of association (binding) of the aptamer with the ligand and the rate of dissociation of the ligand from the aptamer, e.g., by the equilibrium association constant (K) or by its reciprocal, the affinity constant ($K_a$) as is well known in the art. These rates can be determined by methods similar to those commonly used for determining binding kinetics of ligands and receptors or antigens and antibodies, such as, but not limited to, equilibrium assays, competition assays, surface plasmon resonance, and predictive models. The affinity of an aptamer for its ligand can be selected, e.g., during in vitro evolution of the aptamer, or further modified by changes to the aptamer's primary sequence, where such changes can be guided by calculations of binding energy or by algorithms, e.g., as described by Zuker (2003) *Nucleic Acids Res.,* 31:3406-3415 or Bayer and Smolke (2005) *Nature Biotechnol.,* 23:337-343.

The binding state of an aptamer preferably at least partially determines the secondary structure (e.g., the formation of double-stranded or single stranded regions) and the three-dimensional conformation of the aptamer. In embodiments where the recombinant DNA construct further includes DNA that transcribes to regulatory RNA capable of regulating expression of a target sequence, the binding state of the aptamer allosterically affects the conformation of the regulatory RNA and thus the ability of the regulatory RNA to regulate expression of the target sequence.

In one preferred embodiment, the aptamer provides further enhancement of stability to the double-stranded RNA that is transcribed from recombinant DNA constructs of this invention. In one example, the transcribable DNA is transcribed to two RNA regions flanking an aptamer, wherein the two RNA regions form an at least partially double-stranded RNA "stem" between themselves, and wherein the aptamer serves as a "spacer" or "loop" in the resulting structure; such an arrangement is expected to enhance the stability or half-life of the transcript in a manner analogous to that observed for DNA (see, for example, Di Giusto and King (2004) *J. Biol. Chem.,* 279:46483-46489). Transgenic plants having in their genome a recombinant DNA construct that transcribes to such stability-enhanced RNA transcripts are particularly desirable, e.g., where the aptamer or double-stranded RNA or both function to inhibit or kill a pathogen or pest of the transgenic plant.

In other embodiments, recombinant DNA constructs of this invention include DNA that transcribes to RNA for silencing a target gene of a pest or pathogen of a plant, wherein the RNA includes double-stranded RNA and at least one aptamer. In a preferred embodiment, the aptamer serves to direct the double-stranded RNA to its intended target cell or tissues, thereby increasing efficiency of control of the pest or pathogen. In one example, the aptamer directs the dsRNA to the plant tissue to be protected from the pest or pathogen. In another example, the aptamer binds specifically to a tissue, cell, or cell component (such as an epidermal, gut, or surface molecule) of a pest or pathogen of the plant in which the RNA is transcribed. Such targetting by an aptamer results in increased availability of the dsRNA to the targetted cell or tissue, similar to that observed for therapeutically useful aptamer conjugates; see, e.g., Farokhzad et al. (2004) *Cancer Res.,* 64, 7668-7672 and Farokhzad et al. (2006) *Proc. Natl. Acad. Sci. USA,* 103:6315-6320, which disclose RNA aptamers conjugated to controlled-release particles for drug delivery, wherein the RNA aptamers bind to cell-specific antigen, increase uptake of the drug by greater than 70-fold, and result in greatly increased efficacy and decreased toxicity.

Regulatory RNA

In many embodiments, the recombinant DNA construct further includes DNA that transcribes to regulatory RNA capable of regulating expression of a target sequence, wherein the regulation of the target sequence is dependent on the conformation of the regulatory RNA, and the conformation of the regulatory RNA is allosterically affected by the binding state of the RNA aptamer. Such combinations of an aptamer with a regulator RNA domain are commonly known as riboswitches. The regulatory RNA is typically downstream of the aptamer but the two domains may overlap; see, e.g., Najafi-Shoushtari and Famulok (2005) *RNA,* 11:1514-1520 which describes a hairpin ribozyme that includes an aptamer domain and is competitively regulated by flavin mononucleotide and an oligonucleotide complementary to the aptamer domain. In some embodiments, the regulatory RNA is operably linked to the target sequence, and acts "in cis". In other embodiments, the regulatory RNA is not operably linked to the target sequence, and acts "in trans".

In riboswitch embodiments including an aptamer and a regulatory RNA, the riboswitch regulates expression of the target sequence by any suitable mechanism. One non-limiting mechanism is transcriptional regulation by the ligand-dependent formation of an intrinsic terminator stem (an extended stem-loop structure typically followed by a run of 6 or more U residues) that causes RNA polymerase to abort transcription, e.g., before a complete mRNA is formed. In "off" riboswitches, in the absence of sufficient ligand, the unbound aptamer domain permits formation of an "antiterminator stem", which prevents formation of the intrinsic terminator stem and thus allows transcription to proceed; thus, the default state of the riboswitch is "on" (i.e., transcription normally proceeds) and the ligand must be added to turn the riboswitch off. In "on" riboswitches that use this mechanism, the aptamer domain must be in the bound (ligand-occupied) conformation to permit formation of the "antiterminator stem" and allow transcription. Another mechanism is translation regulation, where ligand binding causes structural changes in full-length mRNAs and thereby permits (or prevents) ribosomes from binding to the ribosomal binding site (RBS); the formation of an "anti-anti-RBS" stem and an "anti-RBS" stem is also mutually exclusive. In "on" riboswitches that use this mechanism, absence of the ligand allows formation of an anti-anti-RBS, and thus a structurally unencumbered RBS to which the ribosome can bind. A combination of both transcriptional and translational regulation is also possible. For a detailed discussion of regulation mechanisms, see Mandal and Breaker (2004) *Nature Rev. Mol. Cell Biol.,* 5:451-463.

In some embodiments, the regulatory RNA includes a ribozyme, e.g., a self-cleaving ribozyme, a hammerhead ribozyme, or a hairpin ribozyme. Certain embodiments of the regulatory RNA include RNA sequence that is complementary or substantially complementary to the target sequence. One non-limiting example is where the regulatory RNA includes an anti-sense segment that is complementary or substantially complementary to the target sequence. See, for example, Bayer and Smolke (2005) *Nature Biotechnol.,* 23:337-343, where the regulatory RNA includes both an anti-sense segment complementary to the target sequence, and a sense segment complementary to the anti-sense segment, wherein the anti-sense segment and sense segment are capable of hybridizing to each other to form an intramolecular double-stranded RNA.

In one embodiment, binding of the ligand to the RNA aptamer results in an increase of expression of the target sequence relative to expression in the absence of the binding. In another embodiment, binding of the ligand to the RNA aptamer results in a decrease of expression of the target sequence relative to expression in the absence of the binding.

Some embodiments are characterized by "autoinducibility". In one such embodiment, binding of the ligand to the RNA aptamer results in an increase of expression of the target sequence relative to expression in the absence of the binding, wherein the increase of expression results in a level of the ligand sufficient to maintain the increase of expression. In another embodiment, binding of the ligand to the RNA aptamer results in a decrease of expression of the target sequence relative to expression in the absence of the binding, the decrease of expression resulting in a level of the ligand sufficient to maintain the increase of expression.

Gene Expression Element

The recombinant DNA constructs of the invention can further include a gene expression element. Any gene or genes of interest can be expressed by the gene expression element. Where the gene expression element encodes a protein, such constructs preferably include a functional terminator element to permit transcription and translation of the gene expression element.

The gene of interest to be expressed by the gene expression element can include at least one gene selected from the group consisting of a eukaryotic target gene, a non-eukaryotic target gene, and a microRNA precursor DNA sequence. The gene of interest can include a single gene or multiple genes (such as multiple copies of a single gene, multiple alleles of a single gene, or multiple genes including genes from multiple species). In one embodiment, the gene expression element can include self-hydrolyzing peptide sequences, e.g., located between multiple sequences coding for one or more polypeptides (see, for example, the 2A and "2A-like" self-cleaving sequences from various species, including viruses, trypanosomes, and bacteria, disclosed by Donnelly et al. (2001), *J. Gen. Virol.,* 82:1027-1041). In another embodiment, the gene expression element can include ribosomal "skip" sequences, e.g., located between multiple sequences coding for one or more polypeptides (see, for example, the aphthovirus foot-and-mouth disease virus (FMDV) 2A ribosomal "skip" sequences disclosed by Donnelly et al. (2001), *J. Gen. Virol.,* 82:1013-1025).

A gene of interest can include any coding or non-coding sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a gene expression element include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the plant in which the recombinant DNA construct of the invention is to be transcribed, or can be a non-native gene. A gene of interest can be a marker gene, for example, a selectable marker gene encoding antibiotic, antifungal, or herbicide resistance (e.g., glyphosate or dicamba resistance), or a marker gene encoding an easily detectable trait (e.g., phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention.

Thus, in some embodiments of the invention, the recombinant DNA constructs are designed to silence a target gene of a pest or pathogen of a plant and to simultaneously express at least one gene of interest. In many cases, the gene of interest expresses an insect control agent (e.g., an insecticidal molecule, an insect feeding deterrent, an insect growth, reproductive, or molting inhibitor) or a nematode control agent (e.g., a nematocidal compound, a nematode feeding deterrent, or a nematode growth or reproductive inhibitor).

In one non-limiting example, the recombinant DNA construct is designed for transcription in a maize (*Zea mays*) plant and includes DNA that transcribes to an RNA for silencing a corn rootworm target gene (e.g., a vacuolar ATPase), a gene suppression element for suppressing a endogenous (maize) lysine ketoglutarate reductase/saccharopine dehydrogenase (LKR/SDH) gene, a gene expression element for expressing an exogenous (bacterial) dihydrodipicolinic acid synthase protein, a gene expression element for expressing a *Bacillus thuringiensis* insecticidal endotoxin, and a gene expression element for glyphosate resistance; such a construct would be especially useful for providing glyphosate-resistant maize with enhanced levels of lysine and enhanced resistance to insect pests. In another non-limiting example, the recombinant DNA construct is designed for transcription in a soy (*Glycine max*) plant and includes DNA that transcribes to an RNA for silencing a soybean cyst nematode gene (e.g., a major sperm protein), a gene suppression element for suppressing one or more endogenous (soy) fatty acid dehydrogenases (FAD) gene, and a gene expression element for glyphosate resistance; such a construct would be especially useful for providing glyphosate-resistant soy with enhanced fatty acid composition and enhanced resistance to nematode pests.

T-DNA Borders

T-DNA borders refer to the DNA sequences or regions of DNA that define the start and end of an *Agrobacterium* T-DNA (tumor DNA) and function in cis for transfer of T-DNA into a plant genome by *Agrobacterium*-mediated transformation (see, e.g., Hooykaas and Schilperoort (1992) *Plant Mol. Biol.*, 19:15-38). In one preferred embodiment of the recombinant DNA construct of the invention, the intron in which is embedded the gene suppression element is located between a pair of T-DNA borders, which can be a set of left and right T-DNA borders, a set of two left T-DNA borders, or a set of two right T-DNA borders. In another embodiment, the recombinant DNA construct includes a single T-DNA border and an intron-embedded gene suppression element.

Transgenic Plant Cells, Plants, and Seeds

This invention provides a transgenic plant cell having in its genome a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature.

The transgenic plant cell can be an isolated plant cell (e.g., individual plant cells or cells grown in or on an artificial culture medium), or can be a plant cell in undifferentiated tissue (e.g., callus or any aggregation of plant cells). The transgenic plant cell can be a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules). Further provided is a transgenic plant containing the transgenic plant cell of this invention, that is, a transgenic plant having in its genome a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. The transgenic plant of the invention includes plants of any developmental stage, and includes a regenerated plant prepared from the transgenic plant cells claimed herein, or a progeny plant (which can be an inbred or hybrid progeny plant) of the regenerated plant, or seed of such a transgenic plant. Also provided and claimed is a transgenic seed having in its genome a recombinant DNA construct including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature, and a transgenic plant grown from such transgenic seed.

The transgenic plant cell or transgenic plant of the invention can be any suitable plant cell or plant of interest. Both transiently transformed and stably transformed plant cells are encompassed by this invention. Stably transformed transgenic plants are particularly preferred. In many preferred embodiments, the transgenic plant is a fertile transgenic plant from which seed can be harvested, and the invention further claims transgenic seed of such transgenic plants, wherein the seed preferably also contains the recombinant construct of this invention.

Where a recombinant DNA construct is used to produce a transgenic plant cell or transgenic plant of this invention, transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize), all of which are incorporated by reference.

Another preferred method of plant transformation is *Agrobacterium*-mediated transformation. In one preferred embodiment of the invention, the transgenic plant cell of the invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135, incorporated by reference. Also see De Framond (1983) *Biotechnology*, 1:262-269; and Hoekema et al., (1983) *Nature*, 303:179. In such a binary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 (maize); U.S. Pat. No. 5,981,840 (maize); U.S. Pat. No. 5,463,174 (brassicas), all of which are incorporated by reference. Similar methods have been reported for, among others, peanut (Cheng et al. (1996) *Plant Cell Rep.*, 15: 653); asparagus (Bytebier et al. (1987) *Proc. Natl. Acad. Sci. U.S.A.*, 84:5345); barley (Wan and Lemaux (1994) *Plant Physiol.*, 104:37); rice (Toriyama et al. (1988) *Bio/Technology*, 6:10; Zhang et al. (1988) *Plant Cell Rep.*, 7:379; wheat (Vasil et al. (1992) *Bio/Technology*, 10:667; Becker et al. (1994) *Plant J.*, 5:299), and alfalfa (Masoud et al. (1996) *Transgen. Res.*, 5:313). See also U.S. Patent Application Publication 2003/0167537 A1, incorporated by reference, for a description of vectors, transformation methods, and production of transformed *Arabidopsis thaliana* plants where transcription factors are constitutively expressed by a CaMV35S promoter. Transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microprojectile bombardment). It would be clear to one of skill in the art that various transformation methodologies can be used and modified for production of stable transgenic plants from any number of plant species of interest. All of the above-described patents and publications disclosing materials and methods for plant transformation are incorporated by reference in their entirety.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are incorporated by reference.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047, all of which are incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring the resulting change in expression of the target gene (or concurrent expression of a gene of interest) obtained by transcription of the recombinant construct in the transgenic plant of the invention can be achieved by any suitable methods, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

Other suitable methods for detecting or measuring the resulting change in expression of the target gene (or concurrent expression of a gene of interest) obtained by transcription of the recombinant DNA in the transgenic plant of the invention include measurement of any other trait that is a direct or proxy indication of expression of the target gene (or concurrent expression of a gene of interest) in the transgenic plant in which the recombinant DNA is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., in plants, these assays include plant part assays such as leaf or root assays to determine tolerance of abiotic stress).

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, incorporated by reference.

Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention with one recombinant DNA (effecting change in expression of a target gene) can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a transgenic plant grown from the transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:
(a) plant seeds of the first parent plant (e.g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Nos. 2002/0133852, 2003/0049612, and 2003/0005491, each of which is incorporated by reference in their entirety.

In certain transgenic plant cells and transgenic plants of the invention, it may be desirable to concurrently express (or suppress) a gene of interest while also regulating expression of a target gene. Thus, in some embodiments, the transgenic plant contains recombinant DNA further including a gene expression (or suppression) element for expressing at least one gene of interest, and regulation of expression of a target gene is preferably effected with concurrent expression (or suppression) of the at least one gene of interest in the transgenic plant.

Thus, as described herein, the transgenic plant cells or transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The ultimate goal in plant transformation is to produce plants which are useful to man. In this respect, transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471, incorporated by reference. Thus, this invention also provides commodity products produced from a transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

A transgenic plant having in its genome the recombinant DNA construct of the invention has improved resistance to a pest or pathogen (e.g., insect, nematode, fungal, bacterial, or viral pest or pathogen), relative to a plant lacking in its genome the recombinant DNA construct of the invention, and in preferred embodiments has at least one additional altered trait, relative to a plant lacking said recombinant DNA construct, selected from the group of traits consisting of:

(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen or other nutrients;
(h) modified agronomic characteristics;
(i) modified growth or reproductive characteristics; and
(j) improved harvest, storage, or processing quality.

In particularly preferred embodiments, the transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, transgenic seed, or seed produced by the transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc), carotenoid (e.g., beta-carotene, lycopene, lutein, zeaxanthin, or other carotenoids and xanthophylls), or vitamin (e.g., tocopherols,) composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e.g., peanut allergens including ara h 1, wheat allergens including gliadins and glutenins, soy allergens including P34 allergen, globulins, glycinins, and conglycinins) or of a toxic metabolite (e.g., cyanogenic glycosides in cassava, solanum alkaloids in members of the Solanaceae).

Method of Providing Pest-Resistant Plants

This invention also provides a method of providing a transgenic plant having improved resistance to a pest or pathogen of the plant, including: (a) providing a transgenic plant cell having in its genome a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature, (b) growing a transgenic plant from the transgenic plant cell, and (c) transcribing the recombinant DNA construct in the transgenic plant, thereby conferring improved resistance to the pest or pathogen in the transgenic plant, relative to a plant in which the recombinant DNA construct is not transcribed. The transgenic plant grown from the transgenic plant cell can be directly grown from the transgenic plant cell (e.g., from transformed plant callus), or can be a transgenic progeny plant, including an inbred or hybrid transgenic progeny plant. The transgenic plant can be any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. In a preferred embodiment, the transgenic plant is a crop plant. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The pest or pathogen of the plant is any viral, bacterial, fungal, or invertebrate pest or pathogen. In preferred embodiments, the pest or pathogen is at least one selected from the group consisting of arthropods (including insects and mites), nematodes, and fungi. Non-limiting preferred examples of this invention include a method of providing a transgenic maize plant having improved resistance to a *Diabrotica* species, a method of providing a transgenic soy plant having improved resistance to a soybean cyst nematode, and a method of providing a transgenic soy plant having improved resistance to a soybean rust fungus.

Composition for Providing Pest Resistance

This invention further provides a composition for imparting to a plant resistance to a pest or pathogen of the plant, including an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. In a preferred embodiment, the plant is provided the composition by transcribing in at least a cell of the plant a recombinant DNA construct of this invention, i.e., a recombinant DNA construct for plant transformation including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. In other embodiments, the RNA for silencing a target gene of a pest or pathogen of a plant is produced by biological (e.g., microbiological) or chemical synthesis outside of the plant, and provided to the plant by application, e.g., of a liquid, spray, drench, aerosol, powder, encapsulated formulation, and the like.

In some embodiments, the composition further includes at least one of: (a) cells of the plant; (b) an insect control agent;

and (c) a nematode control agent. Where the composition is provided by transcribing in at least a cell of the plant a recombinant DNA construct of this invention, the composition often includes cells of the plant (generally including the same cells in which the construct is transcribed).

Insect control agents (or, similarly, nematode control agents) include any substance or combination of substances that, when ingested or contacted by a target insect (or nematode), result in the death of the insect (or nematode) or prevent the insect (or nematode) from successful reproduction, or deter the insect (or nematode) from invading or feeding on the plant. Insect control agents (or nematode control agents) thus include any substance or combination of substances that provide protection to the plant from damage by the insect (or nematode). In preferred embodiments, the insect control agent or nematode control agent includes a biologically produced molecule, such as a primary or secondary metabolite ("natural product"); examples include a nucleic acid, polypeptide, enzyme, lipid, lectin, carbohydrate, alkaloid, and the like, particularly phytochemicals or allelochemicals (see, e.g., the review of natural phytochemicals that are antagonistic toward plant-parasitic nematodes by Chitwood (2002), *Ann. Rev. Phytopathol.*, 40:221-249 and the review of transgenically expressed "insect control proteins" including protease inhibitors, alpha-amylase inhibitors, and lectins in Hilder and Boulter (1999) *Crop Protection,* 18:177-191).

Thus, in many embodiments of the invention, the plant is provided the composition by transcribing in at least a cell of the plant a recombinant DNA construct including (a) DNA that transcribes to an RNA for silencing a target gene of a pest or pathogen of a plant, and (b) DNA including a gene expression element for expressing an insect control agent (e.g., an insecticidal molecule, an insect feeding deterrent, an insect growth, reproductive, or molting inhibitor) or a nematode control agent (e.g., a nematocidal compound, a nematode feeding deterrent, or a nematode growth or reproductive inhibitor), or both. In preferred embodiments, the insect control agent or nematode control agent includes a transgenically produced molecule, such as a transgenically expressed primary or secondary metabolite, e.g., proteins, enzymes, lectins, alkaloids, aromatics, or other phytochemicals or allelochemicals. In other embodiments, the plant is provided the composition by transcribing in at least a cell of the plant a recombinant DNA construct including DNA that transcribes to an RNA for silencing a target gene of a pest or pathogen of a plant and by providing to the same or different cells of the plant a separate recombinant DNA construct including a gene expression element for expressing an insect control agent or a nematode control agent.

In one embodiment, the composition includes cells of the plant and an insect control agent, wherein both the double-stranded RNA and the insect control agent impart to the plant resistance to at least one insect pest in common. In another embodiment, the composition includes cells of the plant and a nematode control agent, wherein both the double-stranded RNA and the nematode control agent impart to the plant resistance to at least one nematode pest in common. Where the composition includes both dsRNA and an insect control agent (or nematode control agent), the effects of the dsRNA and the insect control agent (or nematode control agent) are preferably synergistic, that is, the effects of the two provided in combination to the plant are greater than the sum of the effects of the dsRNA plus effects of the insect control agent (or nematode control agent) when provided to the plant separately.

In a non-limiting specific embodiment, the composition includes cells of the plant (e.g., maize root cells) and an insecticidal endotoxin (e.g., a *Bacillus thuringiensis* insecticidal endotoxin). In another non-limiting specific embodiment, the composition includes cells of the plant (e.g., soy root cells) and a nematocidal toxin or a nematode feeding deterrent.

Further provided by this invention is a method of imparting to a plant resistance to a pest or pathogen of the plant, including providing to at least one tissue of the plant a composition for imparting to a plant resistance to a pest or pathogen of the plant, including an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. The composition can be provided to any one or more tissues of the plant, including to specific cells of a given tissue, or to the entire plant. The composition can be provided at any time or times during the plant's growth and development; in some cases it is desirable to provide the composition only at specific times (e.g., at a particular growth or developmental stage), or during periods of biotic or abiotic stress (e.g., during periods of water or temperature stress or during periods of infection or infestation by a pest or pathogen). Specific promoters (see "Promoters" above) are particularly preferred for embodiments where the composition is to be provided by specific temporal or spatial expression of the recombinant DNA construct.

In a non-limiting specific example of the method, the plant is a transgenic maize plant, the pest or pathogen is a *Diabrotica* species, and the transgenic maize plant is provided the composition by transcribing in at least a root cell of the maize plant a recombinant DNA construct including (a) DNA that transcribes to an RNA for silencing a target gene (e.g., a vATPase gene) of the *Diabrotica* species, and (b) DNA including a gene expression element for expressing a *Bacillus thuringiensis* insecticidal endotoxin. In another non-limiting specific example of the method, the plant is a transgenic soy plant, the pest or pathogen is a soybean cyst nematode, and the transgenic soy plant is provided the composition by transcribing in at least a root cell of the soy plant a recombinant DNA construct including (a) DNA that transcribes to an RNA for silencing a target gene (e.g., a vATPase gene) of the soybean cyst nematode (*Heterodera glycines*), and (b) DNA including a gene expression element for expressing a gene or genes for expressing a nematocidal toxin or a nematode feeding deterrent. In yet another non-limiting specific example of the method, the plant is a transgenic soy plant, the pest or pathogen is a soybean rust fungus (*Phakopsora pachyrizi*), and the transgenic soy plant is provided the composition by transcribing in at least a root cell of the soy plant a recombinant DNA construct including (a) DNA that transcribes to an RNA for silencing a target gene (e.g., a fungal tubulin, fungal ATPase, or Pac1 gene) of the soybean rust fungus.

EXAMPLES

Example 1

This example illustrates non-limiting examples of a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. More particularly, this example describes embodiments of the stabilizing feature.

A recombinant DNA construct for plant cell transformation, having transcribable DNA including DNA that transcribes to an RNA for silencing a target gene (vacuolar ATPase) of a pest of a plant (Western corn rootworm, *Diabiotica virgifera virgifera* LeConte), was designed. The transcribable DNA included a region of 558 contiguous nucleotides encoding a double-stranded RNA, and had the sequence AGAAGCCTGGCAATTTCCAAGGT-GATTTTGTCCGTTTCTGCCAGAGATGCTTT ACCTAC-CAGCTGCACAATTTCGGCTAGATCATCT-TCTTCCTGAAGAATTTCCT
TAACTTTGGTTCTAAGAG-
GAATAAACTCTTGGAAGTTTTTGTCATAAAAGTCG
TCCAATGCTCTTAAATATTTGGAATAT-
GATCCAAGCCAGTCTACTGAAGGGA AGTGCT-
TACGTTGGGCAAGaagtactgc-
gatcgcgttaacgctgtgatgtgaaacttgaaattatttgtgttttgat
tgtgattgtgagagtaacggtggcggc-
cgcctgcaggagcCTTGCCCAACGTAAGCACTTCCCTTCA
GTAGACTGGCTTGGATCATATTC-
CAAATATTTAAGAGCATTGGACGACTTTTA TGA-
CAAAAACTTCCAAGAGTTTATTCCTCT-
TAGAACCAAAGTTAAGGAAATT
CTTCAGGAAGAAGATGATCTAGC-
CGAAATTGTGCAGCTGGTAGGTAAAGCAT CTCTG-
GCAGAAACGGACAAAATCACCTTG-
GAAATTGCCAGGCTTCT (SEQ ID NO. 2), wherein nucleotides 1 through 230 encode the anti-sense RNA strand, nucleotides 231 through 328 (indicated by lower case text) encode an RNA spacer, and nucleotides 329 through 558 encode the sense RNA strand. The sense DNA strand, considered separately, includes 230 nucleotides and has the sequence CTTGCCCAACGTAAGCACTTCCCTTCAG-
TAGACTGGCTTGGATCATATTCCAA ATATTTAAGAG-
CATTGGACGACTTTTATGACAAAAACT-
TCCAAGAGTTTATTC
CTCTTAGAACCAAAGTTAAGGAAATTCT-
TCAGGAAGAAGATGATCTAGCCGA AATTGTG-
CAGCTGGTAGGTAAAGCATCTCTGGCA-
GAAACGGACAAAATCACC
TTGGAAATTGCCAGGCTTCT (SEQ ID NO. 3).

Functional asymmetry (ΔΔG) scores for potential siRNAs were calculated for the entire length of the predicted 230 base pair dsRNA. Examples of ΔΔG values are provided in Table 2 for potential siRNAs from a 37-nucleotide region in the sense strand (from nucleotides 352 through 388, indicated by the underlined text given above in SEQ ID NO. 2, or from nucleotides 24 through 60, indicated by the underlined text given above in SEQ ID NO. 3).

TABLE 2

| Nucleotide position in SEQ ID NO. 2 | Nucleotide position in SEQ ID NO. 3 | Reynolds score | Sense 5' minimum free energy | Anti-sense 5' minimum free energy | ΔΔG |
| --- | --- | --- | --- | --- | --- |
| 352-370 | 24-42 | 5 | −7.8 | −9.2 | 1.4 |
| 353-371 | 25-43 | 7 | −9.1 | −9.2 | 0.1 |
| 354-372 | 26-44 | 2 | −7.9 | −9.7 | 1.8 |
| 355-373 | 27-45 | 6 | −7.6 | −8.6 | 1.0 |
| 356-374 | 28-46 | 6 | −8.4 | −7.1 | −1.3 |
| 357-375 | 29-47 | 7 | −8.4 | −7.4 | −1.0 |
| 358-376 | 30-48 | 8 | −8.9 | −5.8 | −3.1 |
| 359-377 | 31-49 | 7 | −9.2 | −4.7 | −4.5 |
| 360-378 | 32-50 | 5 | −9.8 | −6.3 | −3.5 |
| 361-379 | 33-51 | 4 | −11.2 | −8.2 | −3.0 |
| 362-380 | 34-52 | 6 | −11.2 | −9.3 | −1.9 |
| 363-381 | 35-53 | 5 | −10.1 | −9.3 | −0.8 |

TABLE 2-continued

| Nucleotide position in SEQ ID NO. 2 | Nucleotide position in SEQ ID NO. 3 | Reynolds score | Sense 5' minimum free energy | Anti-sense 5' minimum free energy | ΔΔG |
| --- | --- | --- | --- | --- | --- |
| 364-382 | 36-54 | 5 | −9.0 | −7.7 | −1.3 |
| 365-383 | 37-55 | 6 | −8.5 | −5.5 | −3.0 |
| 366-384 | 38-56 | 6 | −9.3 | −4.7 | −4.6 |
| 367-385 | 39-57 | 6 | −9.3 | −4.7 | −4.6 |
| 368-386 | 40-58 | 7 | −9.7 | −4.7 | −5.0 |
| 369-387 | 41-59 | 6 | −8.6 | −4.7 | −3.9 |
| 370-388 | 42-60 | 7 | −7.0 | −4.7 | −2.3 |

The entire length of the predicted 230 bp dsRNA was examined for regions of potential siRNAs that had the strongest positive ΔΔG values, as well as the strongest negative ΔΔG values. Nucleotides were identified that had more positive AG values when located in the 5' end of an anti-sense strand, as compared to the corresponding nucleotide located in the 5' end of a sense strand. For example, comparing the potential siRNAs from the first and last rows of Table 2, a single nucleotide, i.e., the A at position 42 in SEQ ID NO. 3, forms part of the 5'-most base pair of the anti-sense strand complementary to the sequence given by nucleotides 24-42 of SEQ ID NO. 3 and also forms part of the 5'-most base pair of the sense sequence given by nucleotides 42-60 of SEQ ID NO. 3; the A-T base pair formed with the A at position 42 in SEQ ID NO. 3 has a free energy value of 2.6 when it is in the 5'-most base pair in the anti-sense strand and 1.1 when it is in the 5'-most base pair in the sense strand.

Using this approach, nucleotides that were identified as ones that decreased ΔΔG values of an anti-sense siRNA strand were selected as candidates for modification; preferably, modification of these nucleotides did not result in a significant increase in the ΔΔG of the corresponding sense siRNA. Where a nucleotide was modified (e.g., by substitution), it was given a free energy value of zero for all siRNAs where this residue is located within the four 5'-most bases in the sense or anti-sense strands, and the ΔΔG scores were recalculated. In some cases (e.g., "Bumpy-15%" or "Bumpy-25%" described below), attempts were made to decrease the effect of an increase in the sense ΔG by a more dramatic increase in the antisense AG of an siRNA.

Examples of embodiments of the stabilizing features of the RNA transcribed from a recombinant DNA construct of the invention are described below, using as a non-limiting example the recombinant DNA construct including the Western corn rootworm vATPase sequence (SEQ ID NO. 2, including the sense sequence SEQ ID NO. 3). Some of these embodiments included C to A, G to T, A to T, and T to A substitutions in the initial DNA sequence (SEQ ID NO. 2); in these cases, substitutions are identified by the original base (the nucleotide position in SEQ ID NO. 3 where the substitution was made), and the replacement base or bases. In embodiments where deletions were made, each deleted base is identified by its nucleotide position in SEQ ID NO. 3. Introduction of each stabilizing feature was carried out with consideration of the overall effects, with the goal of the resulting population of anti-sense siRNAs being more likely to be incorporated into RISC.

One embodiment of a stabilizing feature includes a mismatch in the double-stranded RNA resulting from substitution of a single base for one base in the sense strand of the double-stranded RNA (see FIG. 1A). Three variants of SEQ ID NO. 2 were made:

(1) "Bumpy-4%": In this variant (SEQ ID NO. 4), a total of nine single base substitutions (C23A, A42T, A63T, C94A, G139T, C166A, C191T, C221T) based on ΔΔG scores were made in the sense strand of the vATPase dsRNA sequence encoded by SEQ ID NO. 2. No more than one single base substitution in a given 21-mer contiguous fragment (potential siRNA) was made.

(2) "Bumpy-15%": In this variant (SEQ ID NO. 5), a total of 34 single base substitutions (C16A, C23A, A32T, C37A, A42T, A52T, C65A, A71T, A74T, C90A, C94A, C107A, C117A, A128T, C133A, A137T, A143T, A146T, A149T, C156A, C166A, G172T, G176T, A183T, C187A, G190T, A192T, G199T, A202T, A208T, G214T, C221A, G225T, C229A) based on ΔΔG scores were made in the sense strand of the vATPase dsRNA sequence encoded by SEQ ID NO. 2. All given 21-mer contiguous fragments (potential siRNAs) had at least one single base substitution in them.

(3) "Bumpy-25%": In this variant (SEQ ID NO. 6), a total of 57 single base substitutions (T2A, A8T, A13T, C16A, C23A, T29A, C33A, C37A, G41T, A45T, C51A, A56T, A60T, A63T, A66T, G70T, G73T, C75A, A80T, C84A, A87T, C90A, C94A, A98T, T100A, A103T, C107A, C109A, A114T, C117A, A124T, G127T, T131A, T134A, G139T, A143T, A146T, C151A, C156A, A160T, C166A, C169A, T173A, T177A, C182A, C187A, C191A, A194T, G199T, A202T, C207A, C210A, A215T, T218A, C221A, G225T, C229A) based on ΔΔG scores were made in the sense strand of the vATPase dsRNA sequence encoded by SEQ ID NO. 2. Almost every potential 21-mer siRNA had a single base substitution in the last 5 bases, as well as elsewhere within the given possible siRNA.

Another embodiment of a stabilizing feature includes a mismatch in the double-stranded RNA resulting from substitution of two bases for one base in the sense strand of the double-stranded RNA (see FIG. 1B). In a non-limiting example using SEQ ID NO. 2, the mismatch was created in the double-stranded RNA by substitution of two bases for one base in the sense strand of the vATPase dsRNA sequence encoded by SEQ ID NO. 2, based on ΔΔG scores, as follows:

"Lumpy-15%": This variant (SEQ ID NO. 7) was based on the same changes as had been made in the "Bumpy-15%" (SEQ ID NO. 5, see above) vATPase sequence, but at each of the 34 substitution sites an extra base (the same nucleotide as the first substituted one) was added. The two-bases-for-one-base substitutions were: C16AA, C23AA, A32TT, C37AA, A42TT, A52TT, C65AA, A71TT, A74TT, C90AA, C94AA, C107AA, C117AA, A128TT, C133AA, A137TT, A143TT, A146TT, A149TT, C156AA, C166AA, G172TT, G176TT, A183TT, C187AA, G190TT, A192TT, G199TT, A202TT, A208TT, G214TT, C221AA, G225TT, C229AA. Thus, as with "Bumpy-15%" (see above), every potential 21-mer siRNA had at least one mismatch.

Another embodiment of a stabilizing feature includes a mismatch in the double-stranded RNA resulting from deletion of a single base in the sense strand of the double-stranded RNA (see FIG. 1C). In a non-limiting example using SEQ ID NO. 2, the mismatch was created in the double-stranded RNA by deletion of a single base in the sense strand of the vATPase dsRNA sequence encoded by SEQ ID NO. 2, based on ΔΔG scores. Two variants were made:

"Looser-15%": In this variant (SEQ ID NO. 8), the bases subject to substitution in the "Bumpy-15%" variant (SEQ ID NO. 5, see above) were deleted. The deletions were: C16, C23, A32, C37, A42, A52, C65, A71, A74, C90, C94, C107, C117, A128, C133, A137, A143, A146, A149, C156, C166, G172, G176, A183, C187, G190, A192, G199, A202, A208, G214, C221, G225, C229. Thus, every potential 21-mer siRNA has at least one deletion.

"Looser-25%": In this variant (SEQ ID NO. 9), the bases subject to substitution in the "Bumpy-25%" variant (SEQ ID NO. 6, see above) were deleted. The deletions were: T2, A8, A13, C16, C23, T29, C33, C37, G41, A45, C51, A56, A60, A63, A66, G70, G73, C75, A80, C84, A87, C90, C94, A98, T100, A103, C107, C109, A114, C117, A124, G127, T131, T134, G139, A143, A146, C151, C156, A160, C166, C169, T173, T177, C182, C187, C191, A194, G199, A202, C207, C210, A215, T218, C221, G225, C229. Thus, almost every potential 21-mer siRNA had a single base substitution in the last 5 bases, as well as elsewhere within the given possible siRNA.

Another embodiment of a stabilizing feature includes a mismatch in the double-stranded RNA resulting from insertion of three or more non-base-paired bases into the sense strand of the double-stranded RNA (see FIG. 1D). In a non-limiting example using SEQ ID NO. 2, the mismatch was created in the double-stranded RNA by insertion of three or more non-base-paired bases in the sense strand of the vATPase dsRNA sequence encoded by SEQ ID NO. 2, as follows:

"Loopy-4%": In this variant (SEQ ID NO. 10), each location (i.e., C23, A42, A63, C94, G139, C166, C191, C221) where in "Bumpy-4%" (SEQ ID NO. 4, see above) a single base substitutions had been made, rather than the single base substitution, a "loop" of nine non-base-paired bases (mainly A's and T's) was inserted. Only one loop per potential 21-mer siRNA was inserted, and some potential 21-mer siRNAs do not have insertions.

Another embodiment of a stabilizing feature includes a mismatch in the double-stranded RNA resulting from insertion of a non-base-paired segment of at least 3 nucleotides in length in both the sense strand and the anti-sense strand of the double-stranded RNA (see FIG. 1E). In a non-limiting example using SEQ ID NO. 2, the mismatch was created in the double-stranded RNA by insertion of three or more non-base-paired bases in the sense strand of the vATPase dsRNA sequence encoded by SEQ ID NO. 2, as follows:

"Bubbles-6": This variant (SEQ ID NO. 11) includes six bubble-shaped regions in the double-stranded RNA, each created by the appropriate substitution of C to G, G to C, A to T, or T to A in the regions including nucleotide positions C23-T29, A61-T67, C93-T102, T134-A141, A174-T184, C209-A217 of SEQ ID NO. 3, resulting in the insertion of a non-base paired segment at these positions. Regions in the original sequence with highly negative ΔΔG values were left intact.

"Bubbles-9": This variant (SEQ ID NO. 12), includes nine bubble-shaped regions in the double-stranded RNA (at the same nine locations where modifications were made in SEQ ID NO. 2 to produce the "Bumpy-4" variant, SEQ ID NO. 4), each created by the appropriate substitution of C to G, G to C, A to T, or T to A in the regions including nucleotide positions C16-T25, G40-T49, A63-C72, A89-A98, A114-T123, A137-A146, T164-T173, G189-G198, G213-C222 of SEQ ID NO. 3, resulting in the insertion of a non-base paired segment at these positions.

Another embodiment of a stabilizing feature includes an RNAse III-resistant stem-loop segment from a tRNA inserted at a terminal part of the double-stranded RNA (see FIG. 1F). Two variants based on SEQ ID NO. 2 were made:

"tRNA Gly": This variant (SEQ ID NO. 13) includes a glycine tRNA sequence added to the 3' terminal part of the sense strand of the vATPase dsRNA sequence encoded by SEQ ID NO. 2.

"tRNA Trp": This variant (SEQ ID NO. 14) includes a tryptophan tRNA sequence added to the 3' terminal part of the sense strand of the vATPase dsRNA sequence encoded by SEQ ID NO. 2.

Recombinant DNA constructs including transcribable DNA including any of the variant sequences (SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, and SEQ ID NO. 14), when transcribed in a plant cell, transcribe to a double-stranded RNA for silencing a target gene (vacuolar ATPase) of a pest of a plant (Western corn rootworm, *Diabrotica virgifera virgifera* LeConte), wherein the double-stranded RNA exhibits improved resistance to a plant RNase III enzyme relative to an RNA lacking the stabilizing feature (i.e., the dsRNA encoded by SEQ ID NO. 2). The predicted folded structures of the RNA transcribed from these variant sequences are depicted as follows: FIG. 2A, dsRNA encoded by SEQ ID NO. 2; FIG. 2B, dsRNA encoded by SEQ ID NO. 4; FIG. 2C, dsRNA encoded by SEQ ID NO. 5; FIG. 2D, dsRNA encoded by SEQ ID NO. 6; FIG. 2E, dsRNA encoded by SEQ ID NO. 7; FIG. 2F, dsRNA encoded by SEQ ID NO. 8; FIG. 2G, dsRNA encoded by SEQ ID NO. 9; FIG. 2H, dsRNA encoded by SEQ ID NO. 10; FIG. 2I, dsRNA encoded by SEQ ID NO. 11; FIG. 2J, dsRNA encoded by SEQ ID NO. 12; FIG. 2K, dsRNA encoded by SEQ ID NO. 13; and FIG. 2L, dsRNA encoded by SEQ ID NO. 14.

In planta stability, that is, resistance to a plant RNase III enzyme is evaluated, e.g., by analyzing the relative amounts of the higher molecular weight RNA species expected to be transcribed from the recombinant DNA constructs, as well as the expected small RNAs (e.g., siRNAs of 21 to 24 base pairs). These recombinant DNA constructs are useful in making transgenic plant cells, plants, and seeds. A preferred embodiment includes a transgenic maize plant that is resistant to Western corn rootworm.

Example 2

This example illustrates a screening technique useful for evaluating the recombinant DNA constructs of the invention. More specifically, this example describes a screen useful for detecting the ability of a double-stranded RNA to silence a target gene (vacuolar ATPase) of a pest of a plant (Western corn rootworm, *Diabrotica virgifera virgifera* LeConte). This bioassay has been previously described, e.g., in International Patent Application Publication WO2005/110068 A2 and US Patent Application Publication US 2006/0021087 A1.

Double-stranded RNA was prepared as follows. The DNA that transcribes to an RNA for silencing a target gene of a pest or pathogen of a plant, wherein the RNA includes double-stranded RNA, was cloned into a plasmid (pBLUESCRIPT KS+) downstream of the T7 promoter. Two micrograms of the plasmid was then linearized with an appropriate enzyme (HindIII) that cut downstream of the cloned DNA. An aliquot of the restriction digest was run on a gel to ensure complete linearization, and the remaining digest reaction was purified with Qiagen's QIAquick PCR purification kit (catalog #28104) and used in Promega's T7 RiboMAX Express RNAi System (catalog #P1700) to synthesize RNA. RNA was synthesized using a reaction mixture containing 10 microliters RiboMAX Express T7 2× Buffer, 2 microliters T7 Express Enzyme Mix, and sufficient linear DNA template and nuclease-free water to make up a 20 microliter final reaction volume (scalable up to 500 microliters if necessary). The RNA synthesis reaction was incubated at 37 degrees Celsius overnight. One microliter RQ1 RNase-free DNase per 20 microliter reaction volume was added and the mixture incubated at 37 degrees Celsius for 30 minutes. One-tenth volume of 3 molar sodium acetate (pH 5.2) and 1 volume of isopropanol was added to the reaction. The reaction was placed on ice for 5 minutes then spun for 10 minutes at maximum speed in a microcentrifuge. The supernatant was removed and the RNA pellet was rinsed with 0.5 milliliters cold 70% ethanol. The pellet was air-dried 10 minutes at room temperature and re-suspended in DEPC water in a volume 2-5 times the original reaction volume. The concentration of RNA was determined by spectrophotometry at a wavelength of 250 nanometers and an aliquot was run on an agarose gel to check for quality.

Samples of double stranded RNA (dsRNA) were subjected to a Western corn rootworm ("WCR", *Diabrotica virgifera virgifera*) bioassay. *Diabrotica virgifera virgifera* (WCR) eggs were obtained from Crop Characteristics, Inc., Farmington, Minn. The non-diapausing WCR eggs were incubated in soil for about 13 days at 24 degrees Celsius, 60% relative humidity, in complete darkness. On or about day 13, the soil containing WCR eggs was placed between #30 and #60 mesh sieves and the eggs were washed out of the soil using a high pressure garden hose. The eggs were surface disinfested by soaking in LYSOL for three minutes, rinsed three times with sterile water, washed one time with a 10% formalin solution and then rinsed three additional times in sterile water. Eggs treated in this way were dispensed onto sterile coffee filters and hatched overnight at 27C, 60% relative humidity, in complete darkness.

Varying doses of double-stranded RNA were applied as an overlay to corn rootworm artificial diet according to the following procedure. Insect diet was prepared essentially as previously described (Pleau et al. (2002) *Entomologia Experimentalis et Applicata*, 105:1-11), with the following modifications. 9.4 grams of SERVA agar was dispensed into 540 milliliters of purified water and agitated until the agar was thoroughly distributed. The water/agar mixture was heated to boiling to completely dissolve the agar, and then poured into a WARING blender. The blender was maintained at low speed while 62.7 grams of BIO-SERV DIET mix (F9757), 3.75 grams lyophilized corn root, 1.25 milliliters of green food coloring, and 0.6 milliliters of formalin was added to the hot agar mixture. The mixture was then adjusted to pH 9.0 with the addition of a 10% potassium hydroxide stock solution. The approximately 600 milliliter volume of liquid diet was continually mixed at high speed and maintained at from about 48 degrees Celsius to about 60 degrees Celsius using a sterilized NALGENE coated magnetic stir bar on a magnetic stirring hot plate while being dispensed in aliquots of 200 microliters into each well of FALCON 96-well round bottom microtiter plates. The diet in the plates was allowed to solidify and air dry in a sterile biohood for about ten minutes.

Thirty (30) microliter volumes of test samples containing either control reagents or double-stranded RNA in varying quantities were overlaid onto the surface of the insect diet in each well using a micro-pipettor repeater. Insect diet was allowed to stand in a sterile biohood for up to one half hour after application of test samples to allow the reagents to diffuse into the diet and to allow the surface of the diet to dry. One WCR neonate larva was deposited in each well with a fine paintbrush. Plates were then sealed with MYLAR and ventilated using an insect pin. 12-72 insect larvae were tested per dose depending on the design of the assay. The bioassay plates were incubated at 27 degrees Celsius, 60% relative humidity in complete darkness for 12-14 days. Stunting was determined by monitoring larval growth (development through instar stages). The number of surviving larvae per dose was recorded at the 12-14 day time point. Larval mass was determined using a suitable microbalance for each surviving larva. Data was analyzed using JMPC$_4$ statistical software (SAS Institute, 1995) and a full factorial ANOVA was conducted with a Dunnet's test to look for treatment effects compared to the untreated control (P<0.05). A Tukey-Kramer post hoc test was performed to compare all pairs of the treatments (P<0.05).

Double-stranded RNA prepared from the variant sequences (SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, and SEQ ID NO. 14) were tested using this bioassay protocol. Results are given in Table 3; N (number of columns of 8 wells assayed) was 5 for all treatments except control wells (N=26), which received 10 millimolar Tris-HCl, pH 7.5; control wells' mean mortality was 8.78 (standard deviation 11.89). Probability values (P) are given for treatments which showed a statistically significant difference from the control.

TABLE 3

Western corn rootworm larval bioassay (mortality results)

| Treatment | 0.001 milligrams per milliliter | | | 0.00005 milligrams per milliliter | | |
|---|---|---|---|---|---|---|
| | Mean | Standard deviation | P | Mean | Standard deviation | P |
| SEQ ID NO. 2 | 19.00 | 12.34 | | 50.36 | 22.32 | <0.0001 |
| SEQ ID NO. 4 | 41.76 | 20.09 | <0.0001 | 31.79 | 13.15 | <0.0001 |
| SEQ ID NO. 5 | 13.00 | 8.18 | | 10.00 | 10.46 | |
| SEQ ID NO. 6 | 6.86 | 9.60 | | 7.50 | 11.18 | |
| SEQ ID NO. 7 | 0.00 | 0.00 | | 8.21 | 7.53 | |
| SEQ ID NO. 8 | 2.50 | 5.59 | | 16.90 | 15.80 | |
| SEQ ID NO. 9 | 0.00 | 0.00 | | 10.83 | 10.87 | |
| SEQ ID NO. 10 | 13.69 | 9.03 | | 9.05 | 8.32 | |
| SEQ ID NO. 11 | 5.83 | 8.12 | | 3.33 | 7.45 | |
| SEQ ID NO. 12 | 3.33 | 7.45 | | 5.71 | 7.82 | |
| SEQ ID NO. 13 | 2.86 | 6.39 | | 70.71 | 19.30 | <0.0001 |
| SEQ ID NO. 14 | 2.50 | 5.59 | | 66.07 | 14.06 | <0.0001 |

In addition to the larval mortality scores shown in Table 3, statistically significant larval stunting (delay in larval development or growth) was observed for SEQ ID NO. 2, SEQ ID NO. 4, SEQ ID NO. 5, SEQ ID NO. 8, SEQ ID NO. 13, and SEQ ID NO. 14 (data not shown). A second set of Western corn rootworm larval bioassays carried out at 0.0005 milligrams per milliliter showed statistically significant larval stunting for SEQ ID NO. 2, SEQ ID NO. 4, SEQ ID NO. 7, SEQ ID NO. 13, and SEQ ID NO. 14 and statistically significant larval mortality for SEQ ID NO. 2, SEQ ID NO. 4, SEQ ID NO. 13, and SEQ ID NO. 14 (data not shown).

Example 3

This example illustrates a non-limiting example of a recombinant DNA construct for plant cell transformation, including transcribable DNA including DNA that transcribes to an RNA for silencing a target gene of a pest or pathogen of a plant, wherein the RNA includes double-stranded RNA and has a stabilizing feature that imparts improved resistance to a plant RNase III enzyme relative to an RNA lacking the stabilizing feature. More specifically, this example describes a stabilizing feature including at least one GC-rich region at a terminal part of the double-stranded RNA, wherein the at least one GC-rich region includes at least 10 base pairs.

One non-limiting embodiment includes DNA that transcribes to a dsRNA with a single double-stranded "stem", having a GC-rich region at one or on both terminal parts of the dsRNA "stem" (see FIG. 3A). Such an RNA can be transcribed from two separate recombinant DNA constructs, or expressed from a single recombinant DNA construct (e.g., using two promoters).

Several embodiments include a single DNA expression cassette as shown in FIGS. 3B, 3C, and 3D, which transcribes to a single RNA transcript including one (e.g., FIGS. 3B and 3C) or multiple (e.g., FIG. 3D) dsRNA "stems". Such a single-transcript dsRNA can include a GC-rich region at one or on both terminal parts of any or all dsRNA "stems". Where there are multiple GC-rich regions serving to "clamp" (thermodynamically stabilize) specific areas of a dsRNA, it is often preferred that each GC-rich region is not complementary to another, to avoid unintentional pairing between strands of different GC-rich regions (see, e.g., FIG. 3C, where "clamp 1" and "clamp 2" are not complementary to each other).

Example 4

This example illustrates a non-limiting example of recombinant DNA constructs of the invention, specifically constructs wherein the stabilizing feature includes multiple double-stranded RNA stems. Such constructs are expected to transcribe to RNA having improved resistance to a plant RNase III enzyme, and thus be particularly useful for controlling a pest or pathogen of a plant in which the construct is transcribed.

FIG. 5G depicts various non-limiting arrangements of double-stranded RNA that can be transcribed from recombinant DNA constructs of the invention. When such double-stranded RNA is formed, it can suppress one or more target genes, and can form a single double-stranded RNA "stem" or multiple double-stranded RNA "stems". Where multiple double-stranded RNA stems are formed, they can be arranged in various shapes, such as "hammerhead" or "barbell" or "dog bone" shapes or "cloverleaf" arrangements.

To form a double-stranded RNA structure resembling a "dog bone", the DNA that transcribes to an RNA for silencing a target gene of a pest or pathogen of a plant is designed to include a single-stranded, contiguous DNA sequence including two non-identical pairs of self-complementary sequences, such that the DNA transcribes to an RNA that also includes two non-identical pairs of self-complementary sequences, which form two separate double-stranded RNA stems. Each member of a non-identical pair of self-complementary sequences preferably includes at least about 19 to about 27 nucleotides (for example 19, 20, 21, 22, 23, or 24 nucleotides) for every target gene that the recombinant DNA construct is intended to suppress; in many embodiments the pair of self-complementary sequence can be larger than at least about 19 to about 27 base pairs (for example, more than about 30, about 50, about 100, about 200, about 300, about 500, about 1000, about 1500, about 2000, about 3000, about 4000, or about 5000 base pairs) for every target gene that the recombinant DNA construct is intended to suppress. Each non-identical pair of self-complementary sequences can be separated by spacer DNA, for example, additional nucleotides that can form a loop connecting the two strands of RNA that form the dsRNA stem (thus forming a stem-loop), or that can connect adjacent dsRNA stems. Spacer DNA can include nucleotides that are located at the distal end of one or both members of the pair of the self-complementary sequences, for example, where inclusion of these nucleotides as "spacer" sequence facilitates the formation of the double-stranded RNA structures, or facilitates the assembly and maintenance of these sequences in plasmids. Spacer DNA can include sequence that itself transcribes to RNA including substantial secondary or tertiary structure, such as RNA that encodes an aptamer.

The non-identical pair of self-complementary sequences can include sequence derived from a single segment of a single target gene, multiple copies of a single segment of a single target gene, multiple segments of a single target gene, segments of multiple target genes, or any combination of these, with or without spacer DNA. Multiple double-stranded RNA stems can be formed in an analogous fashion by including more than two non-identical pairs of self-complementary sequences.

A specific, non-limiting example of this configuration of sequences is shown in FIG. 6, which depicts DNA that transcribes to an RNA for silencing a target gene of a pest or pathogen of a plant (gene suppression element or "GSE", FIG. 6A) useful in recombinant DNA constructs of the invention, and a representation of the type of multiple double-stranded stem RNA that it would be expected to produce (FIG. 6B). The multiple double-stranded stem RNA is depicted with a 3' untranslated region including a polyadenylated tail; however, embodiments of the invention also include analogous constructs that produce a multiple double-stranded stem RNA lacking a polyadenylated tail or a 3' untranslated region. In this example, orientations of the sequences are anti-sense followed by sense for sequence 1, then sense followed by anti-sense for sequence 2 (FIG. 6A). This arrangement may be convenient, e.g., when both sequence 1 and 2 are derived from the same target gene, in which cases the sense sequences can represent sequences that are contiguous in the native target gene. However, any order of sense and anti-sense sequences can be used in the recombinant DNA construct, as long as the transcribed RNA is capable of forming multiple separate double-stranded RNA stems. Analogous recombinant DNA constructs could be designed to provide RNA molecules containing more than 2 double-stranded stems, as shown in FIG. 6C, which depicts an RNA molecule containing 3 double-stranded stems.

Example 5

This example describes a non-limiting embodiment of the recombinant DNA construct of the invention, and methods for its use. More particularly, this example describes a recombinant DNA construct containing a DNA that transcribes to an RNA for silencing a target gene of a pest or pathogen of a plant, wherein the RNA forms multiple double-stranded RNA stems and has improved resistance to a plant RNase III enzyme.

In this non-limiting example, a recombinant DNA construct containing DNA that transcribes to an RNA for silencing a target gene of a pest or pathogen of a plant (gene suppression element, "GSE") was designed to transcribe to an RNA molecule having multiple double-stranded RNA stems similar to that shown in FIG. 6A. In this specific example, the DNA that transcribes to an RNA for silencing a target gene of a pest or pathogen of a plant contained a first sense sequence and second sense sequence (as depicted in FIG. 6A), which are contiguous sequences from SEQ ID NO. 15 (a 872 nucleotide segment of the cDNA sequence of the target gene, vacuolar ATPase gene, of the pest, Western corn root worm, *Diabrotica virgifera virgifera*). However, this method can be used for noncontiguous sequences, including sequences from different genes.

The DNA that transcribes to an RNA for silencing a target gene of a pest or pathogen of a plant, wherein the RNA forms two double-stranded stems similar to that shown in FIG. 6A, included a 1000 nucleotide sequence given as SEQ ID NO. 16. SEQ ID NO. 16 contained nucleotides selected from SEQ ID NO. 15 arranged as follows: the reverse complement of the DNA segment starting at nucleotide 1 and ending at nucleotide 300 of SEQ ID NO. 15, followed by the DNA segment starting at nucleotide 100 and ending at nucleotide 600 of SEQ ID NO. 15, followed by the reverse complement of the DNA segment staring at nucleotide 300 and ending at nucleotide 500 of SEQ ID NO. 15. This DNA (SEQ ID NO. 16) is optionally embedded in a suitable intron (as described above under the heading "Introns") that is operably linked to a suitable promoter (as described above under the heading "Promoters"). Where it is desirable to transcribe RNA that is transported out of the nucleus, a terminator element can be included.

Example 6

This example describes a non-limiting embodiment of the recombinant DNA construct of the invention, and methods for its use in providing transgenic plant cells and transgenic plants. More particularly, this example describes a recombinant DNA construct containing a DNA that transcribed to an RNA for silencing a target gene (vacuolar ATPase) of a pest or pathogen of a plant (corn root worm), wherein the RNA formed multiple double-stranded RNA stems, had improved resistance to a plant RNase III enzyme, and was effective in silencing the target gene.

A recombinant DNA construct ("pMON100806") was designed to include a 668 base pair DNA (SEQ ID NO. 17) that transcribes to an RNA for silencing a target gene of a pest or pathogen of a plant (corn root worm vacuolar ATPase), wherein the RNA forms two double-stranded stems in a "barbell" or "dog bone" shape (similar to FIG. 6B). As a control, another recombinant DNA construct ("pMON94805") was designed to include a 558 base pair DNA (SEQ ID NO. 18) that transcribes to an RNA for silencing a target gene of a pest or pathogen of a plant (corn root worm vacuolar ATPase), wherein the RNA forms a single double-stranded stem or inverted repeat. Each recombinant DNA construct was introduced by *Agrobacterium*-mediated transformation into LH244 maize (*Zea mays*) plant cells, and transgenic maize plants were grown from the transformed maize cells.

Figure 7:
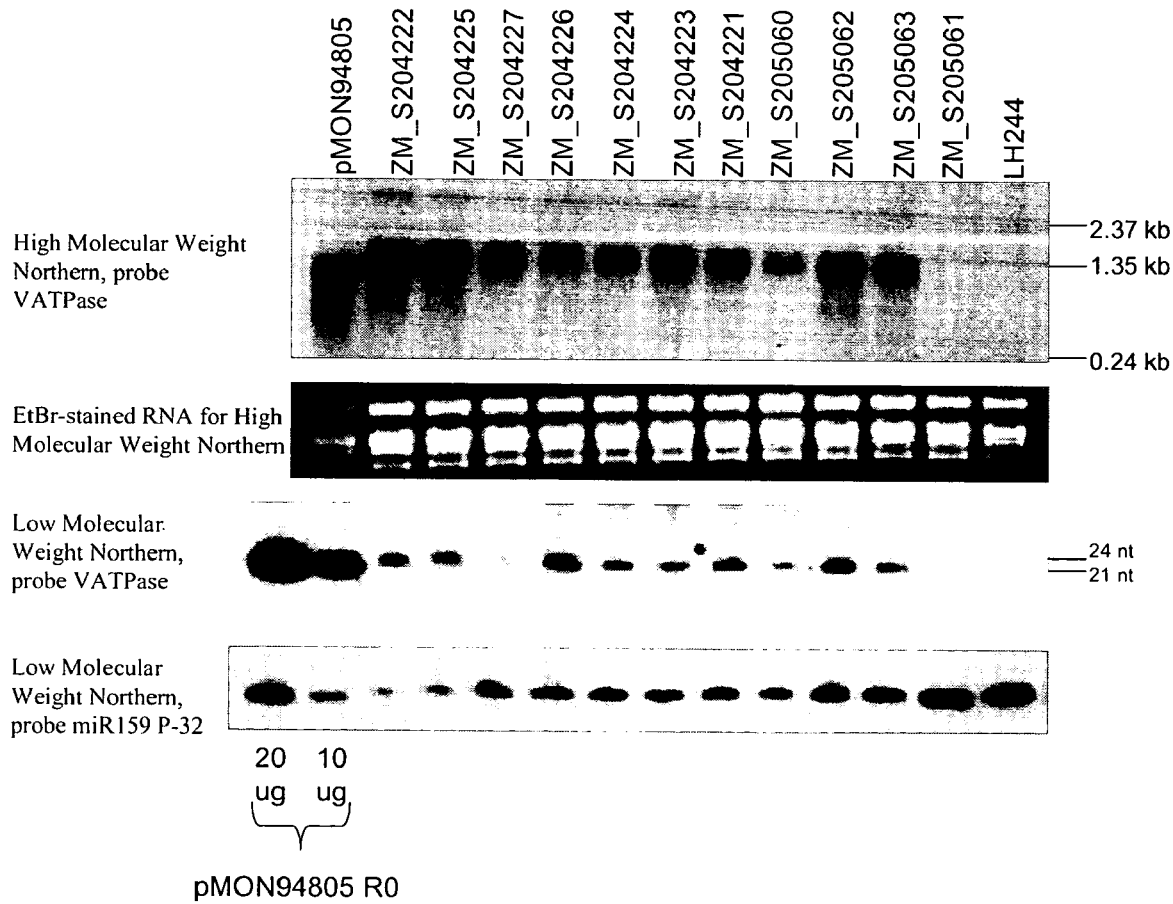
FIGS. 7 and 8 depict high molecular weight and low molecular weight Northern blots of RNA isolated from transgenic maize plants (R0 events) having in their genome a recombinant DNA construct containing a DNA that transcribed to an RNA for silencing a target gene (corn root worm vacuolar ATPase), wherein the RNA formed multiple double-stranded RNA stems, had improved resistance to a plant RNase III enzyme, and was effective in silencing the target gene. Experimental details are provided in Example 6. Ten micrograms of RNA were loaded per lane, except as noted. Lanes are labelled with the individual R0 event identifier (beginning with "ZM_S"). High molecular weight Northern blots have molecular weight markers indicated on the right. Low molecular weight Northern blots indicate the position of small RNAs having 21 or 24 nucleotides ("nt"), respectively; these blots were also probed for an abundant microRNA (miR159). LH244, control (non-transgenic) maize plant. Blots showing ethidium bromide-stained RNA are included to verify lane loading. Abbreviations: "EtBr", ethidium bromide.
Figure 8:
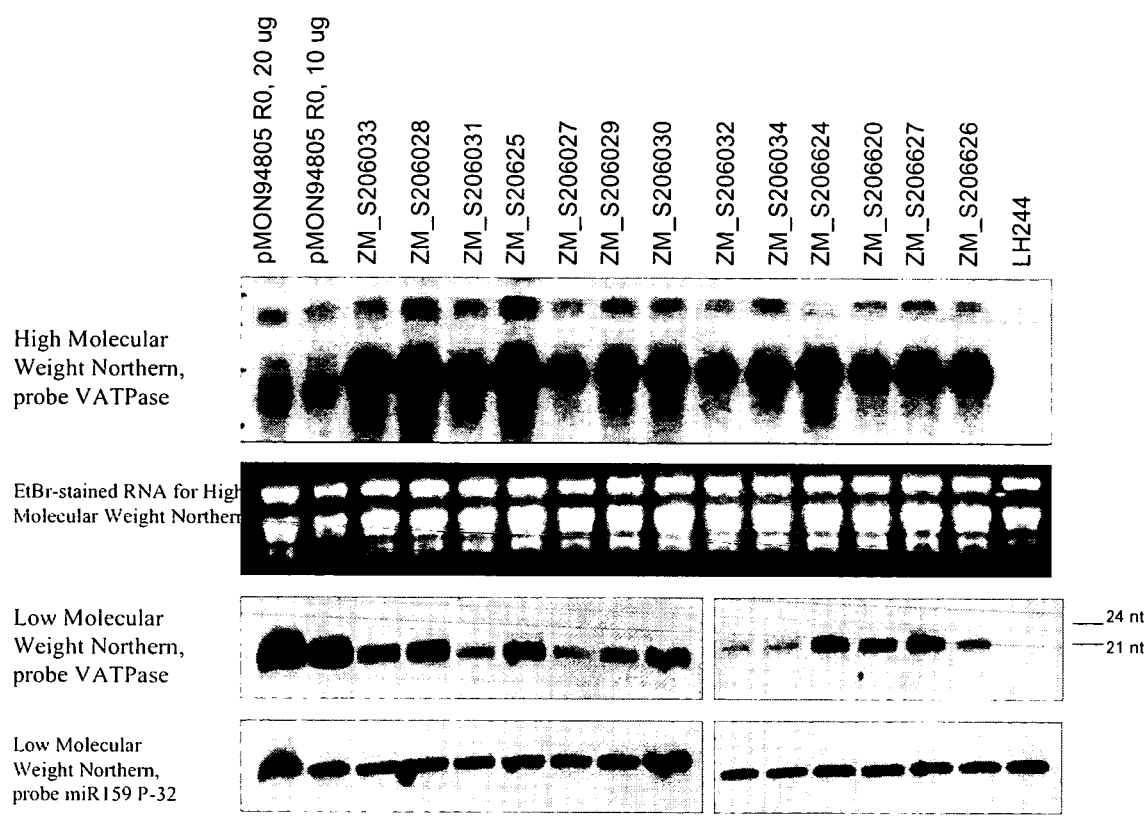

RNA was isolated from several transgenic maize plants (R0 events) and analyzed by Northern blot (FIGS. 7 and 8). FIGS. 7 and 8 depict high molecular weight and low molecular weight Northern blots for RNA isolated from several pMON100806 R0 events (lanes labelled with the event identifier beginning with "ZM_S"); the control was RNA isolated from pMON94805 R0 events (ZM_S176336 in FIG. 7, and ZM_S176333 for high molecular weight, and ZM_S176336 for low molecular weight in FIG. 8). As a low molecular weight control, the blots were also probed for an abundant small RNA (miR159). In both sets of Northern blots, there was increased abundance of the high molecular weight RNA and decreased abundance of small RNAs (about 21 to about 24 nucleotides) from the multiple double-stranded stem SEQ ID NO. 17, when compared to the single double-stranded stem control (SEQ ID NO. 18). The results indicate that SEQ ID NO. 17, which transcribes to an RNA with a stabilizing feature (multiple double-stranded stems), was resistant to plant RNase III enzymes and was processed less frequently to small RNAs in a maize plant cell, relative to an RNA lacking the stabilizing feature (an RNA with only one double-stranded stem, which is transcribed from SEQ ID NO. 18).

Transgenic maize plants containing a recombinant DNA construct described in this example are anticipated to have resistance to corn rootworm, relative to plants lacking the construct. This is supported by results from a corn rootworm larval bioassay. Double-stranded RNAs for suppressing corn rootworm vacuolar ATPase were prepared from (a) DNA (SEQ ID NO. 17) that transcribes to a multiple double-stranded RNA stem and from (b) DNA (SEQ ID NO. 19, contained in construct pIC17504) that is flanked by T7 promoters on both the 5' and 3' sides and transcribes to a single double-stranded RNA stem. The dsRNAs were tested using a corn rootworm larval bioassay, as described in Example 2. Results are given in Table 4; N (number of columns of 8 wells assayed) was 5 for all treatments except control wells (N=2), which received 10 millimolar Tris-HCl, pH 7.5; control wells' mean mortality was 0.00 (standard deviation 0.00). Treatments with either the multiple double-stranded stem RNA (transcribed from SEQ ID NO. 17) or the single double-stranded stem RNA (transcribed from SEQ ID NO. 19) showed a statistically significant difference in larval mortality compared to the control.

TABLE 4

Western corn rootworm larval bioassay (mortality results)

| Treatment | 0.001 milligrams per milliliter | |
|---|---|---|
| | Mean | Standard deviation |
| SEQ ID NO. 17 (multiple dsRNA stems) | 81.67 | 12.36 |
| SEQ ID NO. 19 (single dsRNA stem) | 85.00 | 14.91 |

In addition to the larval mortality scores shown in Table 4, statistically significant larval stunting (delay in larval development or growth) was observed for the multiple double-stranded stem sequence (SEQ ID NO. 17) as well as the single double-stranded stem (SEQ ID NO. 19) (data not shown).

Example 7

This example describes non-limiting embodiments of the recombinant DNA construct of the invention. More particularly, this example describes a recombinant DNA construct containing a DNA that transcribed to an RNA for silencing a target gene (vacuolar ATPase) of a pest or pathogen of a plant (corn root worm), wherein the RNA formed multiple double-stranded RNA stems arranged in pseudoknots or having "kissing stem-loop" structures; see, for example, Staple and Butcher (2005) *PLoS Biol.*, 3(6):e213. These RNAs are expected to have improved resistance to a plant RNase III enzyme, and to be effective in silencing the target gene.

Various multiple double-stranded stem embodiments were designed based on the single double-stranded stem sequence encoded in the control recombinant DNA construct ("pMON94805"), which includes a 558 base pair DNA (SEQ ID NO. 18) (see Example 6).

Figure 9:
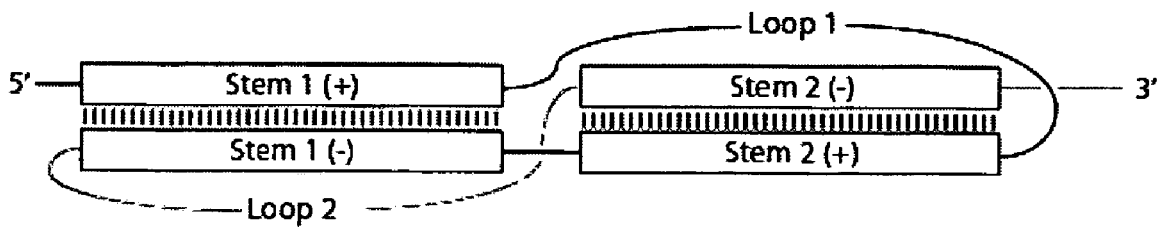
FIG. 9 depicts additional embodiments including multiple double-stranded RNA stems as described in detail in Example 7.
Figure 9:
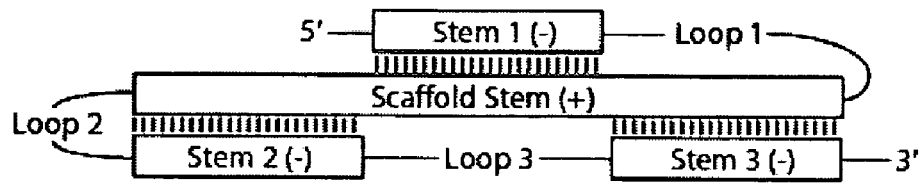
Figure 9:
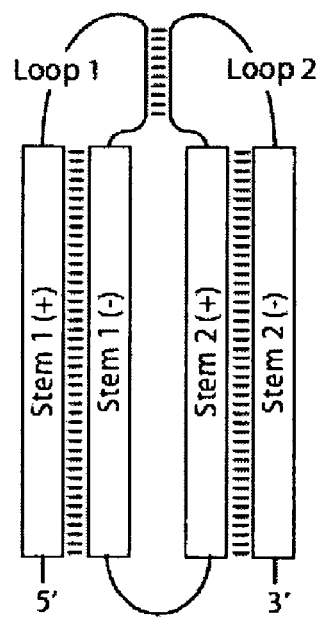

One non-limiting embodiment is contained in SEQ ID NO. 20, which is predicted to form a two-stem or "H-type" pseudoknot and contains the following regions corresponding to those shown in FIG. 9A:

Stem 1 (+): SEQ ID NO. 21
Loop 1: SEQ ID NO. 22
Stem 2 (+): SEQ ID NO. 23
Stem 1 (−): SEQ ID NO. 24
Loop 2: SEQ ID NO. 25
Stem 2 (−): SEQ ID NO. 26

Another non-limiting embodiment is contained in SEQ ID NO. 27, which is predicted to form a three-stem pseudoknot and contains the following regions corresponding to those shown in FIG. 9B:

Stem 1 (−): SEQ ID NO. 28
Loop 1: SEQ ID NO. 29
Scaffold stem (+): SEQ ID NO. 30
Loop 2: SEQ ID NO. 31
Stem 2 (−): SEQ ID NO. 32
Loop 3: SEQ ID NO. 33
Stem 3 (−): SEQ ID NO. 34

Yet another non-limiting embodiment is contained in SEQ ID NO. 35, which is predicted to form a structure having "kissing stem loops", and contains the following regions corresponding to those shown in FIG. 9C:

Stem 1 (+): SEQ ID NO. 36
Loop 1: SEQ ID NO. 37
Stem 1 (−): SEQ ID NO. 38
Stem 2 (+): SEQ ID NO. 39
Loop 2: SEQ ID NO. 40
Stem 2 (−): SEQ ID NO. 41

The (+) and (−) symbols in the above non-limiting examples indicate sense and anti-sense, respectively. However, it would be apparent to one of ordinary skill in the art that many variations on the above illustrated examples are possible. For example, the order of sense and anti-sense sequences can be reversed, so long as the ability to form dsRNA is maintained; spacer or loop sequence can include additional sense or anti-sense sequence; and additional elements (e.g., ribozymes or aptamers) can be incorporated.

Recombinant DNA constructs containing SEQ ID NO. 20, SEQ ID NO. 27, or SEQ ID NO. 35 are transformed into maize plant cells; transgenic maize plants grown from these transformed cells are resistant to corn rootworm, relative to plants lacking the construct.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A recombinant DNA construct for plant cell transformation, comprising transcribable DNA that transcribes to a single RNA for silencing one or more target genes of a pest or pathogen of a plant, said DNA comprising operably linked two or more non-identical pairs of self-complementary sequences of said target genes, wherein said RNA comprises double-stranded RNA and has a stabilizing feature comprising multiple double-stranded RNA stems, said multiple double-stranded RNA stems comprising two or more non-identical pairs of self-complementary sequences, said stabilizing feature imparting improved resistance to a plant Dicer or Dicer-like enzyme relative to an RNA lacking said stabilizing feature, and wherein said one or more target genes of a pest or pathogen of a plant comprises a vacuolar ATPase gene, wherein the construct comprises SEQ ID NO:16 or SEQ ID NO: 17, wherein said pest or pathogen of a plant is a *Diabrotica* species.

2. The recombinant DNA construct of claim 1, further comprising at least one of:
   (a) a plant promoter
   (b) a ribozyme flanking said transcribable DNA;
   (c) an intron, in which said transcribable DNA is embedded;
   (d) DNA that transcribes to an RNA aptamer capable of binding to a ligand;
   (e) DNA that transcribes to an RNA aptamer capable of binding to a ligand and DNA that transcribes to regulatory RNA capable of regulating expression of a target sequence, wherein said regulation is dependent on the conformation of said regulatory RNA, and said conformation of said regulatory RNA is allosterically affected by the binding state of said RNA aptamer;
   (f) at least one gene expression element; and
   (g) at least one T-DNA border.

3. A transgenic plant cell having in its genome the recombinant DNA construct of claim 1.

4. A transgenic plant containing the transgenic plant cell of claim 3.

5. Transgenic seed having in its genome the recombinant DNA construct of claim 1.

6. A method of providing a transgenic plant having improved resistance to a pest or pathogen of said plant, comprising:
   (a) providing the transgenic plant cell of claim 3,
   (b) growing a transgenic plant from said transgenic plant cell, and
   (c) transcribing said recombinant DNA construct in said transgenic plant,
   thereby conferring improved resistance to said pest or pathogen in said transgenic plant, relative to a plant in which said recombinant DNA construct is not transcribed.

7. The method of claim 6, wherein said transgenic plant is a transgenic maize plant and said *Diabrotica* species is Western corn rootworm.

8. A method of imparting to a plant resistance to a pest or pathogen of said plant, comprising
   (a) transforming said plant with the recombinant DNA construct of claim 1;
   (b) transcribing said recombinant DNA construct in said transformed plant; and
   (c) providing to at least one tissue of said transformed plant at least one of an insect control agent or a nematode control agent,
   thereby imparting to said transformed plant resistance to a pest or pathogen of said plant.

9. The method of claim 8, wherein said plant is a transgenic maize plant, and said *Diabrotica* species is Western corn rootworm.

10. The recombinant DNA construct of claim 1, comprising operably linked multiple anti-sense DNA segments that are anti-sense to at least one segment of one of said one or more target genes and multiple sense DNA segments that are the same as at least one segment of one of said one or more target genes, and wherein when said recombinant DNA construct is transcribed to a single RNA, said multiple anti-sense DNA segments and the multiple sense DNA segments are transcribed to form multiple double-stranded RNA stems.

11. The recombinant DNA construct of claim 10, wherein said multiple double-stranded stems are arranged to form at least one structure selected from the group consisting of a two-stem structure and a three or more-stem structure.

12. The recombinant DNA construct of claim 10, further comprising spacer DNA segments, wherein said spacer DNA segments are located between multiple anti-sense DNA segments or multiple sense DNA segments, and said spacer DNA segments are located within double-stranded stems when said transcribable DNA is transcribed to an RNA.

13. The recombinant DNA construct of claim 10, further comprising spacer DNA segments, wherein said spacer DNA segments are located between a base-pairing anti-sense DNA segment and a sense DNA segment, and said spacer DNA segments are located outside of double-stranded stems when said transcribable DNA is transcribed to an RNA.

14. The recombinant DNA construct of claim 13, wherein said spacer DNA segments form a loop region of sense or of anti-sense or of unrelated RNA sequence, separating a pair of inverted repeats.

15. The recombinant DNA construct of claim 10, comprising an anti-sense DNA segment followed by a sense DNA segment for a first target gene, and a sense DNA segment followed by an anti-sense DNA segment for a second target gene, wherein said first and second target genes are either the same or different.

16. The recombinant DNA construct of claim 15, further comprising a first spacer DNA segment between said anti-sense DNA segment and sense DNA segment for the first target gene, and a second spacer DNA segment between said sense DNA segment and anti-sense DNA segment for the second target gene, wherein said first and second spacer DNA segments form a first and second loop when transcribed.

17. Progeny of a transgenic plant according to claim 4, said progeny having in its genome said recombinant DNA construct.

18. The method of claim 8, wherein said resistance to a pest or pathogen of said plant is greater than the sum of
 (a) resistance obtained by transcribing in at least one cell of said plant DNA that transcribes to RNA for silencing a target gene of a pest or pathogen of a plant, wherein said RNA comprises double-stranded RNA and has a stabilizing feature comprising multiple double-stranded RNA stems, said stabilizing feature imparting improved resistance to a plant Dicer or Dicer-like enzyme relative to an RNA lacking said stabilizing feature, and
 (b) resistance obtained by providing to at least one tissue of said plant at least one of an insect control agent or a nematode control agent.

19. The method of claim 9, wherein said at least one of an insect control agent comprises a Bacillus thuringiensis insecticidal endotoxin.

20. The recombinant DNA construct of claim 11, wherein said two stem structure is selected from the group consisting of a hammerhead structure, a barbell structure, a dog bone structure, and a structure having "kissing stem loops".

21. The recombinant DNA construct of claim 11, wherein said three or more stem structure is selected from the group consisting of a cloverleaf structure and a pseudoknot-like structure.

22. The recombinant DNA construct of claim 10, comprising in operable linkage a first anti-sense DNA segment, a first spacer DNA segment, a first sense DNA segment, a second sense DNA segment, a second spacer DNA segment, and a second anti-sense DNA segment, wherein transcription of said recombinant DNA construct produces a first double-stranded RNA stem for suppressing a first target gene and a second double-stranded RNA stem for suppressing a second target gene.

23. The recombinant DNA construct of claim 10, comprising in operable linkage a first anti-sense DNA segment, a first spacer DNA segment, a first sense DNA segment for a first sequence of said one or more target genes, a second sense DNA segment, a second spacer DNA segment, and a second anti-sense DNA segment for a second sequence of said one or more target genes, wherein transcription of said recombinant DNA construct produces two double-stranded RNA stems for suppressing said one or more target genes.

24. The recombinant DNA construct of claim 1, wherein said *Diabrotica* species is Western corn root worm.

25. A recombinant DNA construct comprising operably linked multiple anti-sense DNA segments that are anti-sense to multiple target sequences of a vacuolar ATPase gene and multiple sense DNA segments that are the same as said multiple target sequences, wherein when said recombinant DNA construct is transcribed to a single RNA, said multiple anti-sense DNA segments and the multiple sense DNA segments are transcribed to form multiple double-stranded RNA stems comprising two or more non-identical pairs of self-complementary sequences of said vacuolar ATPase gene wherein the construct comprises SEQ ID NO:16 or SEQ ID NO: 17.

26. A transgenic plant cell comprising in its genome the recombinant DNA construct of claim 25.

27. A transgenic plant containing the transgenic plant cell of claim 26.

28. Transgenic seed comprising in its genome the recombinant DNA construct of claim 25.

29. The recombinant DNA construct of claim 24, further comprising SEQ ID NO: 20, SEQ ID NO: 27 or SEQ ID NO: 35.

* * * * *

UNITED STATES PATENT AND TRADEMARK OFFICE
CERTIFICATE OF CORRECTION

| | | |
|---|---|---|
| PATENT NO. | : 8,404,927 B2 | Page 1 of 1 |
| APPLICATION NO. | : 11/453155 | |
| DATED | : March 26, 2013 | |
| INVENTOR(S) | : Allen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Thirtieth Day of December, 2014

Michelle K. Lee
*Deputy Director of the United States Patent and Trademark Office*

SEQUENCE LISTING

<160> NUMBER OF SEQ ID NOS: 46

<210> SEQ ID NO 1
<211> LENGTH: 19
<212> TYPE: DNA
<213> ORGANISM: Artificial Sequence
<220> FEATURE:
<223> OTHER INFORMATION: synthetic construct

<400> SEQUENCE: 1
gatctagccg aaattgtgc                                                        19

<210> SEQ ID NO 2
<211> LENGTH: 558
<212> TYPE: DNA
<213> ORGANISM: Artificial Sequence
<220> FEATURE:
<223> OTHER INFORMATION: synthetic construct

<400> SEQUENCE: 2
agaagcctgg caatttccaa ggtgattttg tccgtttctg ccagagatgc tttacctacc            60
agctgcacaa tttcggctag atcatcttct tcctgaagaa tttccttaac tttggttcta          120
agaggaataa actcttggaa gttttgtca taaaagtcgt ccaatgctct taaatatttg           180
gaatatgatc caagccagtc tactgaaggg aagtgcttac gttgggcaag aagtactgcg          240
atcgcgttaa cgctgtgatg tgaaacttga aattatttgt gttttgattg tgattgtgag          300
agtaacggtg gcggccgcct gcaggagcct tgcccaacgt aagcacttcc cttcagtaga          360
ctggcttgga tcatattcca aatatttaag agcattggac gacttttatg acaaaaactt          420
ccaagagttt attcctctta gaaccaaagt taaggaaatt cttcaggaag aagatgatc           480 agccgaaatt gtgcagctgg taggtaaagc atctctggca gaaacggaca aaatcacctt          540
ggaaattgcc aggcttct                                                       558

<210> SEQ ID NO 3
<211> LENGTH: 230
<212> TYPE: DNA
<213> ORGANISM: Artificial Sequence
<220> FEATURE:
<223> OTHER INFORMATION: synthetic construct

<400> SEQUENCE: 3
cttgcccaac gtaagcactt cccttcagta gactggcttg gatcatattc caaatatttta          60 agagcattgg acgactttta tgacaaaaac ttccaagagt ttattcctct tagaaccaaa          120
gttaaggaaa ttcttcagga agaagatgat ctagccgaaa ttgtgcagct ggtaggtaaa          180
gcatctctgg cagaaacgga caaaatcacc ttggaaattg ccaggcttct                     230

<210> SEQ ID NO 4
<211> LENGTH: 558
<212> TYPE: DNA
<213> ORGANISM: Artificial Sequence
<220> FEATURE:
<223> OTHER INFORMATION: synthetic construct

<400> SEQUENCE: 4
agaagcctgg caatttccaa ggtgattttg tccgtttctg ccagagatgc tttacctacc            60
agctgcacaa tttcggctag atcatcttct tcctgaagaa tttccttaac tttggttcta          120
agaggaataa actcttggaa gttttgtca taaaagtcgt ccaatgctct taaatatttg           180

```
gaatatgatc caagccagtc tactgaaggg aagtgcttac gttgggcaag aagtactgcg    240
atcgcgttaa cgctgtgatg tgaaacttga aattatttgt gttttgattg tgattgtgag    300
agtaacggtg gcggccgcct gcaggagcct tgcccaacgt aagcacttcc attcagtaga    360
ctggcttggt tcatattcca aatatttaag tgcattggac gacttttatg acaaaaactt    420
caaagagttt attcctctta gaacaaaagt taaggaaatt cttcagtaag aagatgatct    480
agccgaaatt gtgaagctgg taggtaaagc atctctggaa gaaacggaca aaatcacctt    540
ggaaattgac aggcttct                                                  558
```

<210> SEQ ID NO 5
<211> LENGTH: 558
<212> TYPE: DNA
<213> ORGANISM: Artificial Sequence
<220> FEATURE:
<223> OTHER INFORMATION: synthetic construct

<400> SEQUENCE: 5

```
agaagcctgg caatttccaa ggtgattttg tccgtttctg ccagagatgc tttacctacc     60
agctgcacaa tttcggctag atcatcttct tcctgaagaa tttccttaac tttggttcta    120
agaggaataa actcttggaa gtttttgtca taaaagtcgt ccaatgctct aaatatttg     180 gaatatgatc caagccagtc tactgaaggg aagtgcttac gttgggcaag aagtactgcg    240
atcgcgttaa cgctgtgatg tgaaacttga aattatttgt gttttgattg tgattgtgag    300
agtaacggtg gcggccgcct gcaggagcct tgcccaacgt aagaacttcc attcagtagt    360
ctggattggt tcatattcct aatatttaag agaattggtc gtcttttatg acaaaaaatt    420
caaagagttt attcatctta gaacaaaagt taaggtaatt attctggaag tagttgttct    480
agcagaaatt gtgaagctgt tagttaaagc ttctatgtct gaaacgtact aaatctcctt    540
gtaaattgac agtcttat                                                  558
```

<210> SEQ ID NO 6
<211> LENGTH: 558
<212> TYPE: DNA
<213> ORGANISM: Artificial Sequence
<220> FEATURE:
<223> OTHER INFORMATION: synthetic construct

<400> SEQUENCE: 6

```
agaagcctgg caatttccaa ggtgattttg tccgtttctg ccagagatgc tttacctacc     60
agctgcacaa tttcggctag atcatcttct tcctgaagaa tttccttaac tttggttcta    120
agaggaataa actcttggaa gtttttgtca taaaagtcgt ccaatgctct aaatatttg     180 gaatatgatc caagccagtc tactgaaggg aagtgcttac gttgggcaag aagtactgcg    240
atcgcgttaa cgctgtgatg tgaaacttga aattatttgt gttttgattg tgattgtgag    300
agtaacggtg gcggccgcct gcaggagcca tgccctacgt agaacttcc attcagaaga     360 atggattgta tcttattcaa aatttttag tgctttgtaa gactttttg aaaataaatt      420 acaagtgatt tttcatatta gtacaaaagt ttagtaaaat catcagtaag tagttgatat    480
agcagaattt gtgaagatgg aaggaaaaga atctatggaa gtaacgtact aaataacatt    540
ggtaaatgac agtcttat                                                  558
```

<210> SEQ ID NO 7
<211> LENGTH: 591
<212> TYPE: DNA
<213> ORGANISM: Artificial Sequence
<220> FEATURE:

<223> OTHER INFORMATION: synthetic construct

<400> SEQUENCE: 7

| agaagcctgg caatttccaa ggtgattttg tccgtttctg ccagagatgc tttacctacc | 60 |
| agctgcacaa tttcggctag atcatcttct tcctgaagaa tttccttaac tttggttcta | 120 |
| agaggaataa actcttggaa gtttttgtca taaaagtcgt ccaatgctct taaatatttg | 180 |
| gaatatgatc caagccagtc tactgaaggg aagtgcttac gttgggcaag aagtactgcg | 240 |
| atcgcgttaa cgctgtgatg tgaaacttga aattatttgt gttttgattg tgattgtgag | 300 |
| agtaacggtg gcggccgcct gcaggagcct tgcccaacgt aagaaacttc caattcagta | 360 |
| gttctggaat tggtttcata ttccttaata tttaagagaa attggttcgt tcttttatga | 420 |
| caaaaaatt caaagagtt tattcaatct tagaacaaaa agttaaggtt aattaattct | 480 |
| tggaagttag tttgtttcta gcaagaaatt gtgaaagctg tttagtttaa agctttctaa | 540 |
| tgttcttgaa acgttactta aatcttcctt gttaaattga acagttctta a | 591 |

<210> SEQ ID NO 8
<211> LENGTH: 524
<212> TYPE: DNA
<213> ORGANISM: Artificial Sequence
<220> FEATURE:
<223> OTHER INFORMATION: synthetic construct

<400> SEQUENCE: 8

| agaagcctgg caatttccaa ggtgattttg tccgtttctg ccagagatgc tttacctacc | 60 |
| agctgcacaa tttcggctag atcatcttct tcctgaagaa tttccttaac tttggttcta | 120 |
| agaggaataa actcttggaa gtttttgtca taaaagtcgt ccaatgctct taaatatttg | 180 |
| gaatatgatc caagccagtc tactgaaggg aagtgcttac gttgggcaag aagtactgcg | 240 |
| atcgcgttaa cgctgtgatg tgaaacttga aattatttgt gttttgattg tgattgtgag | 300 |
| agtaacggtg gcggccgcct gcaggagcct tgcccaacgt aagacttcct tcagtagctg | 360 |
| gttggtcata ttccaatatt taagagattg gcgcttttat gacaaaaatt caagagttta | 420 |
| ttctcttaga acaaagttaa ggaattttcg gaagagtgtc tagcgaaatt gtgagctgta | 480 |
| gtaaagctct tgcgaaacga caaatcccctt gaaattgcag cttt | 524 |

<210> SEQ ID NO 9
<211> LENGTH: 503
<212> TYPE: DNA
<213> ORGANISM: Artificial Sequence
<220> FEATURE:
<223> OTHER INFORMATION: synthetic construct

<400> SEQUENCE: 9

| agaagcctgg caatttccaa ggtgattttg tccgtttctg ccagagatgc tttacctacc | 60 |
| agctgcacaa tttcggctag atcatcttct tcctgaagaa tttccttaac tttggttcta | 120 |
| agaggaataa actcttggaa gtttttgtca taaaagtcgt ccaatgctct taaatatttg | 180 |
| gaatatgatc caagccagtc tactgaaggg aagtgcttac gttgggcaag aagtactgcg | 240 |
| atcgcgttaa cgctgtgatg tgaaacttga aattatttgt gttttgattg tgattgtgag | 300 |
| agtaacggtg gcggccgcct gcaggagcct gcccacgtag acttccttca gagatggttg | 360 |
| atctattcaa attttaggct tgagactttt tgaaaaattc aaggttttct ttagacaaag | 420 |
| ttagaaatct cagaagagtg attagcgaat tgtgagtgga ggaaagatct tggagaacgt | 480 |
| acaaatactt ggaatgcagc ttt | 503 |

<210> SEQ ID NO 10
<211> LENGTH: 639
<212> TYPE: DNA
<213> ORGANISM: Artificial Sequence
<220> FEATURE:
<223> OTHER INFORMATION: synthetic construct

<400> SEQUENCE: 10

```
agaagcctgg caatttccaa ggtgattttg tccgtttctg ccagagatgc tttacctacc      60
agctgcacaa tttcggctag atcatcttct tcctgaagaa tttccttaac tttggttcta     120
agaggaataa actcttggaa gttttgtca taaaagtcgt ccaatgctct taaatatttg      180
gaatatgatc caagccagtc tactgaaggg aagtgcttac gttgggcaag aagtactgcg     240
atcgcgttaa cgctgtgatg tgaaacttga aattatttgt gttttgattg tgattgtgag     300
agtaacggtg gcggccgcct gcaggagcct tgcccaacgt aagcacttcc catcatcatc     360
tcagtagact ggcttggaat atatatatca tattccaaat atttaagatt attattagca     420
ttggacgact tttatgacaa aaacttccca tcatcataag agtttattcc tcttagaacc     480
tgatgatgaa aagttaagga aattcttcag gaaatttaaa aagaagatga tctagccgaa     540
attgtgcaga gagagaagct ggtaggtaaa gcatctctgg ctaataataa agaaacggac     600
aaaatcacct tggaaattgc aaaaattttt caggcttct                            639
```

<210> SEQ ID NO 11
<211> LENGTH: 558
<212> TYPE: DNA
<213> ORGANISM: Artificial Sequence
<220> FEATURE:
<223> OTHER INFORMATION: synthetic construct

<400> SEQUENCE: 11

```
agaagcctgg caatttccaa ggtgattttg tccgtttctg ccagagatgc tttacctacc      60
agctgcacaa tttcggctag atcatcttct tcctgaagaa tttccttaac tttggttcta     120
agaggaataa actcttggaa gttttgtca taaaagtcgt ccaatgctct taaatatttg      180
gaatatgatc caagccagtc tactgaaggg aagtgcttac gttgggcaag aagtactgcg     240
atcgcgttaa cgctgtgatg tgaaacttga aattatttgt gttttgattg tgattgtgag     300
agtaacggtg gcggccgcct gcaggagcct tgcccaacgt aagcacttcc gaagtcaaga     360
ctggcttgga tcatattcca aatatttatc tcgtatggac gactttatg acaaaaactt      420
ggttctcaaa attcctctta gaaccaaagt taaggaaatt caagtccttg aagatgatct     480
agccgaaatt gtgcagctgg ttccatttcg atctctggca gaaacggaca aaatcaggaa     540
ccttttttgcc aggcttct                                                  558
```

<210> SEQ ID NO 12
<211> LENGTH: 540
<212> TYPE: DNA
<213> ORGANISM: Artificial Sequence
<220> FEATURE:
<223> OTHER INFORMATION: synthetic construct

<400> SEQUENCE: 12

```
agaagcctgg caatttccaa ggtgattttg tccgtttctg ccagagatgc tttacctacc      60
agctgcacaa tttcggctag atcatcttct tcctgaagaa tttccttaac tttggttcta     120
agaggaataa actcttggaa gttttgtca taaaagtcgt ccaatgctct taaatatttg      180
gaatatgatc caagccagtc tactgaaggg aagtgcttac gttgggcaag aagtactgcg     240
```

```
atcgcgttaa cgctgtgatg tgaaacttga aattatttgt gttttgattg tgattgtgag    300
agtaacggtg gcggccgcct gcaggagcct tgcccaacgt aaggtgaagg gaacagtaga    360
ctggcttcct agtataacca aatatttaag tcgtaacctg gacttttatg acaaaatgaa    420
gattctgttt attcctctta gttgatttca aaaggaaatt cttctctttc ttcttgatct    480
agccgaaatt gacatcgacc aaggtaaagc atctctccat cttttgcgaca aaatcacctt    540
```

<210> SEQ ID NO 13
<211> LENGTH: 629
<212> TYPE: DNA
<213> ORGANISM: Artificial Sequence
<220> FEATURE:
<223> OTHER INFORMATION: synthetic construct

<400> SEQUENCE: 13

```
agaagcctgg caatttccaa ggtgattttg tccgtttctg ccagagatgc tttacctacc    60
agctgcacaa tttcggctag atcatcttct tcctgaagaa tttccttaac tttggttcta    120
agaggaataa actcttggaa gttttgtca taaaagtcgt ccaatgctct aaatatttg    180 gaatatgatc caagccagtc tactgaaggg aagtgcttac gttgggcaag aagtactgcg    240
atcgcgttaa cgctgtgatg tgaaacttga aattatttgt gttttgattg tgattgtgag    300
agtaacggtg gcggccgcct gcaggagcct tgcccaacgt aagcacttcc cttcagtaga    360
ctggcttgga tcatattcca aatatttaag agcattggac gactttatg acaaaaactt    420 ccaagagttt attcctctta gaaccaaagt taaggaaatt cttcaggaag aagatgatct    480
agccgaaatt gtgcagctgg taggtaaagc atctctggca gaaacggaca aaatcacctt    540
ggaaattgcc aggcttctgc accagtggtc tagtggtaga atagtaccct gccacggtac    600
agacccgggt tcgattcccg gctggtgca                                      629
```

<210> SEQ ID NO 14
<211> LENGTH: 630
<212> TYPE: DNA
<213> ORGANISM: Artificial Sequence
<220> FEATURE:
<223> OTHER INFORMATION: synthetic construct

<400> SEQUENCE: 14

```
agaagcctgg caatttccaa ggtgattttg tccgtttctg ccagagatgc tttacctacc    60
agctgcacaa tttcggctag atcatcttct tcctgaagaa tttccttaac tttggttcta    120
agaggaataa actcttggaa gttttgtca taaaagtcgt ccaatgctct aaatatttg    180 gaatatgatc caagccagtc tactgaaggg aagtgcttac gttgggcaag aagtactgcg    240
atcgcgttaa cgctgtgatg tgaaacttga aattatttgt gttttgattg tgattgtgag    300
agtaacggtg gcggccgcct gcaggagcct tgcccaacgt aagcacttcc cttcagtaga    360
ctggcttgga tcatattcca aatatttaag agcattggac gactttatg acaaaaactt    420 ccaagagttt attcctctta gaaccaaagt taaggaaatt cttcaggaag aagatgatct    480
agccgaaatt gtgcagctgg taggtaaagc atctctggca gaaacggaca aaatcacctt    540
ggaaattgcc aggcttctgg atccgtggcg caatggtagc gcgtctgact ccagatcaga    600
aggttgcgtg ttcgattcac gtcgggttca                                     630
```

<210> SEQ ID NO 15
<211> LENGTH: 872
<212> TYPE: DNA
<213> ORGANISM: Diabrotica virgifera

<400> SEQUENCE: 15

```
gcaagtatgg cctgtacgtc aagcaaggcc agtcagtgaa aaattacctg ccaaccatcc      60
tctgcttaca ggacagcgtg tacttgatgc tcttttccca tgtgtacagg gtggtactac     120
tgccattccc ggagctttcg gttgtggaaa aactgtaatt tcacaatctc tttccaaata     180
ttccaactct gatgtcatta tctacgtcgg ttgcggagaa agaggtaacg aaatgtctga     240
agtattgaga gatttccctg aattgactgt tgaaattgac gggcacactg aatctattat     300
gaaacgtacc gcattggtcg ccaacacatc taacatgcct gtagctgctc gtgaagcttc     360
tatctatact ggtattactc tttctgaata cttccgtgat atgggttaca acgtatctat     420
gatggctgac tcgacatcac gttgggccga agctttgaga gaaatttcag gtcgtttggc     480
tgaaatgcct gccgattccg gttatccggc ttacttaggt gcccgtttgg cttccttcta     540
cgaacgtgct ggtcgcgtta aatgtttagg taatccagac agagaaggat ccgtttcaat     600
tgtaggagcc gtatcacctc ctggtggtga tttctcagat cctgttacca ctgctactct     660
tggtattgta caggtgttct ggggtttgga caagaaactt gcccaacgta agcacttccc     720
ttcagtagac tggcttggat catattccaa atatttaaga gcattggacg acttttatga     780
caaaaacttc caagagtttta ttcctcttag aaccaaagtt aaggaaattc ttcaggaaga     840
agatgatcta gccgaaattg tgcagctggt ag                                    872
```

<210> SEQ ID NO 16
<211> LENGTH: 1000
<212> TYPE: DNA
<213> ORGANISM: Artificial Sequence
<220> FEATURE:
<223> OTHER INFORMATION: synthetic construct

<400> SEQUENCE: 16

```
ataatagatt cagtgtgccc gtcaatttca acagtcaatt cagggaaatc tctcaatact      60
tcagacattt cgttacctct ttctccgcaa ccgacgtaga taatgacatc agagttggaa     120
tatttggaaa gagattgtga aattacagtt tttccacaac cgaaagctcc gggaatggca     180
gtagtaccac cctgtacaca tgggaaaaga gcatcaagta cacgctgtcc tgtaagcaga     240
ggatggttgg caggtaattt ttcactgact ggccttgctt gacgtacagg ccatacttgc     300
tgtgtacagg gtggtactac tgccattccc ggagctttcg gttgtggaaa aactgtaatt     360
tcacaatctc tttccaaata ttccaactct gatgtcatta tctacgtcgg ttgcggagaa     420
agaggtaacg aaatgtctga agtattgaga gatttccctg aattgactgt tgaaattgac     480
gggcacactg aatctattat gaaacgtacc gcattggtcg ccaacacatc taacatgcct     540
gtagctgctc gtgaagcttc tatctatact ggtattactc tttctgaata cttccgtgat     600
atgggttaca acgtatctat gatggctgac tcgacatcac gttgggccga agctttgaga     660
gaaatttcag gtcgtttggc tgaaatgcct gccgattccg gttatccggc ttacttaggt     720
gcccgtttgg cttccttcta cgaacgtgct ggtcgcgtta aatgtttagg taatccagac     780
agagaaggat ccgtttcaat cggaatcggc aggcatttca gccaaacgac ctgaaatttc     840
tctcaaagct tcggcccaac gtgatgtcga gtcagccatc atagatacgt tgtaacccat     900
atcacggaag tattcagaaa gagtaatacc agtatagata gaagcttcac gagcagctac     960
aggcatgtta gatgtgttgg cgaccaatgc ggtacgtttc                          1000
```

<210> SEQ ID NO 17
<211> LENGTH: 668
<212> TYPE: DNA

```
<213> ORGANISM: Artificial Sequence
<220> FEATURE:
<223> OTHER INFORMATION: synthetic construct

<400> SEQUENCE: 17
ttctaagagg aataaactct tggaagtttt tgtcataaaa gtcgtccaat gctcttaaat      60
atttggaata tgatccaagc cagtctactg aagggaagtg cttacgttgg gcaagaagta     120
ctgcgatcgc gttaacgctg tgatgtgaaa cttgaaatta tttgtgtttt gattgtgatt     180
gtgagagtaa cggtggcggc cgcctgcagg agcggtaccc ttgcccaacg taagcacttc     240
ccttcagtag actggcttgg atcatattcc aaatatttaa gagcattgga cgactttat      300
gacaaaaact tccaagagtt tattcctctt agaaccaaag ttaaggaaat tcttcaggaa     360
gaagatgatc tagccgaaat tgtgcagctg gtaggtaaag catctctggc agaaacggac     420
aaaatcacct ggaaattgc caggcttcta agctaattac aacctcaacc tgagaaacaa      480
gatctgaaag cttccaata tcagcaacat caagctgggt agcagttgta ttttcaatac      540
catcaacgtc gacagaagcc tggcaatttc caaggtgatt ttgtccgttt ctgccagaga     600
tgctttacct accagctgca aatttcggc tagatcatct tcttcctgaa gaatttcctt      660
aactttgg                                                              668

<210> SEQ ID NO 18
<211> LENGTH: 558
<212> TYPE: DNA
<213> ORGANISM: Artificial Sequence
<220> FEATURE:
<223> OTHER INFORMATION: synthetic construct

<400> SEQUENCE: 18
agaagcctgg caatttccaa ggtgattttg tccgtttctg ccagagatgc tttacctacc      60
agctgcacaa tttcggctag atcatcttct tcctgaagaa tttccttaac tttggttcta     120
agaggaataa actcttggaa gttttgtca taaaagtcgt ccaatgctct taaatatttg      180
gaatatgatc caagccagtc tactgaaggg aagtgcttac gttgggcaag aagtactgcg     240
atcgcgttaa cgctgtgatg tgaaacttga aattatttgt gttttgattg tgattgtgag     300
agtaacggtg gcggccgcct gcaggagcct tgcccaacgt aagcacttcc cttcagtaga     360
ctggcttgga tcatattcca aatatttaag agcattggac gactttttatg acaaaaactt     420
ccaagagttt attcctctta gaaccaaagt taaggaaatt cttcaggaag aagatgatct     480
agccgaaatt gtgcagctgg taggtaaagc atctctggca gaaacggaca aaatcacctt     540
ggaaattgcc aggcttct                                                   558

<210> SEQ ID NO 19
<211> LENGTH: 765
<212> TYPE: DNA
<213> ORGANISM: Artificial Sequence
<220> FEATURE:
<223> OTHER INFORMATION: synthetic construct

<400> SEQUENCE: 19
gttcaaaaca gaacaattac actacatttta ttgattctaa caatctaata gatgttataa      60
gatactcgtt tatcttaatc tgtacaatta actttaattg ggtaatgtaa tatacaagat     120
taaagggta aagaaaaaat ttaaaacaat ttacatgaag aaaaccaagt aatactgaaa      180
atataaacga tattaagcac ctgtatatatt aaaaaagtat taaaacgaaa aaacttaata     240
gtaattggaa tggcgggaaa aatgtttaaa aagtatttaa taagcactgt accctcaccc     300
```

-continued

| aaaaaaacta tacacatatt caacaattta cataatttat tttgtacagg ataatatcaa | 360 |
| aaaagagaaa acctatcttt agttactatc tttagtacgg ccatattaat attcacagaa | 420 |
| gtgagggata gaggccttat tattctttt gataaatatc gctatatttt taaacttaca | 480 |
| ctgatgaaca aaataggaaa atttccttaa aaagatttaa tcttctaagt ttctgaaggc | 540 |
| ctgctgaata tcttcatata attgatcaaa atctgccttg attttagctt caccatcttt | 600 |
| tacgggatcc ttaaatttca tactgctaag ttgatataaa attccactca ttgaatctct | 660 |
| tattacgttc caagtgatct tattttctga ttgtgcggtt gattctacag cgtgtctcgc | 720 |
| catgtcgtac aaaccgatca tgtttctcaa cataccgaca gtttt | 765 |

<210> SEQ ID NO 20
<211> LENGTH: 558
<212> TYPE: DNA
<213> ORGANISM: Artificial Sequence
<220> FEATURE:
<223> OTHER INFORMATION: synthetic construct

<400> SEQUENCE: 20

| agaagcctgg caatttccaa ggtgattttg tccgtttctg ccagagatgc tttacctacc | 60 |
| agctgcacaa tttcggctag atcatcttct tcctgaagaa tttccttaac tttggaagta | 120 |
| ctgcgatcgc gttaacgctg tgatgtgaaa cttgaaatta tttgttctaa gaggaataaa | 180 |
| ctcttggaag tttttgtcat aaaagtcgtc caatgctctt aaatatttgg aatatgatcc | 240 |
| aagccagtct actgaaggga agtgcttacg ttgggcaagc caaagttaag gaaattcttc | 300 |
| aggaagaaga tgatctagcc gaaattgtgc agctggtagg taaagcatct ctggcagaaa | 360 |
| cggacaaaat caccttggaa attgccaggc ttcttgtttt gattgtgatt gtgagagtaa | 420 |
| cggtggcggc cgcctgcagg agccttgccc aacgtaagca cttcccttca gtagactggc | 480 |
| ttggatcata ttccaaatat ttaagagcat tggacgactt ttatgacaaa aacttccaag | 540 |
| agtttattcc tcttagaa | 558 |

<210> SEQ ID NO 21
<211> LENGTH: 115
<212> TYPE: DNA
<213> ORGANISM: Artificial Sequence
<220> FEATURE:
<223> OTHER INFORMATION: synthetic construct

<400> SEQUENCE: 21

| agaagcctgg caatttccaa ggtgattttg tccgtttctg ccagagatgc tttacctacc | 60 |
| agctgcacaa tttcggctag atcatcttct tcctgaagaa tttccttaac tttgg | 115 |

<210> SEQ ID NO 22
<211> LENGTH: 49
<212> TYPE: DNA
<213> ORGANISM: Artificial Sequence
<220> FEATURE:
<223> OTHER INFORMATION: synthetic construct

<400> SEQUENCE: 22

| aagtactgcg atcgcgttaa cgctgtgatg tgaaacttga aattatttg | 49 |

<210> SEQ ID NO 23
<211> LENGTH: 115
<212> TYPE: DNA
<213> ORGANISM: Artificial Sequence
<220> FEATURE:
<223> OTHER INFORMATION: synthetic construct

<400> SEQUENCE: 23
ttctaagagg aataaactct tggaagtttt tgtcataaaa gtcgtccaat gctcttaaat    60
atttggaata tgatccaagc cagtctactg aagggaagtg cttacgttgg gcaag       115

<210> SEQ ID NO 24
<211> LENGTH: 115
<212> TYPE: DNA
<213> ORGANISM: Artificial Sequence
<220> FEATURE:
<223> OTHER INFORMATION: synthetic construct

<400> SEQUENCE: 24
ccaaagttaa ggaaattctt caggaagaag atgatctagc cgaaattgtg cagctggtag    60
gtaaagcatc tctggcagaa acggacaaaa tcaccttgga aattgccagg cttct       115

<210> SEQ ID NO 25
<211> LENGTH: 49
<212> TYPE: DNA
<213> ORGANISM: Artificial Sequence
<220> FEATURE:
<223> OTHER INFORMATION: synthetic construct

<400> SEQUENCE: 25
tgttttgatt gtgattgtga gagtaacggt ggcggccgcc tgcaggagc              49

<210> SEQ ID NO 26
<211> LENGTH: 115
<212> TYPE: DNA
<213> ORGANISM: Artificial Sequence
<220> FEATURE:
<223> OTHER INFORMATION: synthetic construct

<400> SEQUENCE: 26
cttgcccaac gtaagcactt cccttcagta gactggcttg gatcatattc caaatattta    60
agagcattgg acgacttta tgacaaaaac ttccaagagt ttattcctct tagaa         115

<210> SEQ ID NO 27
<211> LENGTH: 558
<212> TYPE: DNA
<213> ORGANISM: Artificial Sequence
<220> FEATURE:
<223> OTHER INFORMATION: synthetic construct

<400> SEQUENCE: 27
ttatgacaaa aacttccaag agtttattcc tcttagaacc aaagttaagg aaattcttca    60
ggaagaagat gatctaaagt actgcgatcg cgttaacgct gtgatgtgaa gaagcctggc   120
aatttccaag gtgattttgt ccgtttctgc cagagatgct ttacctacca gctgcacaat   180
ttcggctaga tcatcttctt cctgaagaat ttccttaact ttggttctaa gaggaataaa   240
ctcttggaag ttttgtcat aaaagtcgtc caatgctctt aaatatttgg aatatgatcc   300
aagccagtct actgaaggga gtgcttacg ttgggcaaga acttgaaatt atttgtgttt   360
tgattgtgat tcttgcccaa cgtaagcact tcccttcagt agactggctt ggatcatatt   420
ccaaatattt aagagcattg acgacttgt gagagtaacg gtggcggccg cctgcaggag   480
cgccgaaatt gtgcagctgg taggtaaagc atctctggca gaaacggaca aaatcacctt   540
ggaaattgcc aggcttct                                                558

<210> SEQ ID NO 28
<211> LENGTH: 76
<212> TYPE: DNA

```
<213> ORGANISM: Artificial Sequence
<220> FEATURE:
<223> OTHER INFORMATION: synthetic construct

<400> SEQUENCE: 28
ttatgacaaa aacttccaag agtttattcc tcttagaacc aaagttaagg aaattcttca      60
ggaagaagat gatcta                                                     76

<210> SEQ ID NO 29
<211> LENGTH: 33
<212> TYPE: DNA
<213> ORGANISM: Artificial Sequence
<220> FEATURE:
<223> OTHER INFORMATION: synthetic construct

<400> SEQUENCE: 29
aagtactgcg atcgcgttaa cgctgtgatg tga                                  33

<210> SEQ ID NO 30
<211> LENGTH: 230
<212> TYPE: DNA
<213> ORGANISM: Artificial Sequence
<220> FEATURE:
<223> OTHER INFORMATION: synthetic construct

<400> SEQUENCE: 30
agaagcctgg caatttccaa ggtgattttg tccgtttctg ccagagatgc tttacctacc      60
agctgcacaa tttcggctag atcatcttct cctgaagaa tttccttaac tttggttcta     120
agaggaataa actcttggaa gttttgtca taaaagtcgt ccaatgctct taaatatttg     180
gaatatgatc caagccagtc tactgaaggg aagtgcttac gttgggcaag                230

<210> SEQ ID NO 31
<211> LENGTH: 32
<212> TYPE: DNA
<213> ORGANISM: Artificial Sequence
<220> FEATURE:
<223> OTHER INFORMATION: synthetic construct

<400> SEQUENCE: 31
aacttgaaat tatttgtgtt ttgattgtga tt                                   32

<210> SEQ ID NO 32
<211> LENGTH: 77
<212> TYPE: DNA
<213> ORGANISM: Artificial Sequence
<220> FEATURE:
<223> OTHER INFORMATION: synthetic construct

<400> SEQUENCE: 32
cttgcccaac gtaagcactt cccttcagta gactggcttg gatcatattc caaatattta      60
agagcattgg acgactt                                                    77

<210> SEQ ID NO 33
<211> LENGTH: 33
<212> TYPE: DNA
<213> ORGANISM: Artificial Sequence
<220> FEATURE:
<223> OTHER INFORMATION: synthetic construct

<400> SEQUENCE: 33
gtgagagtaa cggtggcggc cgcctgcagg agc                                  33

<210> SEQ ID NO 34
```

```
<211> LENGTH: 77
<212> TYPE: DNA
<213> ORGANISM: Artificial Sequence
<220> FEATURE:
<223> OTHER INFORMATION: synthetic construct

<400> SEQUENCE: 34
gccgaaattg tgcagctggt aggtaaagca tctctggcag aaacggacaa aatcaccttg    60
gaaattgcca ggcttct                                                  77

<210> SEQ ID NO 35
<211> LENGTH: 502
<212> TYPE: DNA
<213> ORGANISM: Artificial Sequence
<220> FEATURE:
<223> OTHER INFORMATION: synthetic construct

<400> SEQUENCE: 35
ttctaagagg aataaactct tggaagtttt tgtcataaaa gtcgtccaat gctcttaaat    60
atttggaata tgatccaagc cagtctactg aagggaagtg cttacgttgg gcaagaagta   120
ctgcgatcgc gttaaccttg cccaacgtaa gcacttccct tcagtagact ggcttggatc   180
atattccaaa tatttaagag cattggacga cttttatgac aaaaacttcc aagagtttat   240
tcctcttaga accaaagtta aggaaattct tcaggaagaa gatgatctag ccgaaattgt   300
gcagctggta ggtaaagcat ctctggcaga aacggacaaa atcaccttgg aaattgccag   360
gcttctgctg tggcgatcgc agtgaaaaga agcctggcaa tttccaaggt gattttgtcc   420
gtttctgcca gagatgcttt acctaccagc tgcacaattt cggctagatc atcttcttcc   480
tgaagaattt ccttaacttt gg                                            502

<210> SEQ ID NO 36
<211> LENGTH: 115
<212> TYPE: DNA
<213> ORGANISM: Artificial Sequence
<220> FEATURE:
<223> OTHER INFORMATION: synthetic construct

<400> SEQUENCE: 36
ttctaagagg aataaactct tggaagtttt tgtcataaaa gtcgtccaat gctcttaaat    60
atttggaata tgatccaagc cagtctactg aagggaagtg cttacgttgg gcaag       115

<210> SEQ ID NO 37
<211> LENGTH: 21
<212> TYPE: DNA
<213> ORGANISM: Artificial Sequence
<220> FEATURE:
<223> OTHER INFORMATION: synthetic construct

<400> SEQUENCE: 37
aagtactgcg atcgcgttaa c                                             21

<210> SEQ ID NO 38
<211> LENGTH: 115
<212> TYPE: DNA
<213> ORGANISM: Artificial Sequence
<220> FEATURE:
<223> OTHER INFORMATION: synthetic construct

<400> SEQUENCE: 38
cttgcccaac gtaagcactt cccttcagta gactggcttg gatcatattc caaatattta    60
agagcattgg acgactttta tgacaaaaac ttccaagagt ttattcctct tagaa       115
```

-continued

<210> SEQ ID NO 39
<211> LENGTH: 115
<212> TYPE: DNA
<213> ORGANISM: Artificial Sequence
<220> FEATURE:
<223> OTHER INFORMATION: synthetic construct

<400> SEQUENCE: 39
ccaaagttaa ggaaattctt caggaagaag atgatctagc cgaaattgtg cagctggtag    60
gtaaagcatc tctggcagaa acggacaaaa tcaccttgga aattgccagg cttct         115

<210> SEQ ID NO 40
<211> LENGTH: 21
<212> TYPE: DNA
<213> ORGANISM: Artificial Sequence
<220> FEATURE:
<223> OTHER INFORMATION: synthetic construct

<400> SEQUENCE: 40
gctgtggcga tcgcagtgaa a                                               21

<210> SEQ ID NO 41
<211> LENGTH: 115
<212> TYPE: DNA
<213> ORGANISM: Artificial Sequence
<220> FEATURE:
<223> OTHER INFORMATION: synthetic construct

<400> SEQUENCE: 41
agaagcctgg caatttccaa ggtgattttg tccgtttctg ccagagatgc tttacctacc    60
agctgcacaa tttcggctag atcatcttct tcctgaagaa tttccttaac tttgg         115

<210> SEQ ID NO 42
<211> LENGTH: 18
<212> TYPE: RNA
<213> ORGANISM: Artificial Sequence
<220> FEATURE:
<223> OTHER INFORMATION: sense strand of "Loopy" dsRNA

<400> SEQUENCE: 42
ggacuuuuua aaaacguu                                                   18

<210> SEQ ID NO 43
<211> LENGTH: 16
<212> TYPE: RNA
<213> ORGANISM: Artificial Sequence
<220> FEATURE:
<223> OTHER INFORMATION: sense strand of "Bubbles" dsRNA

<400> SEQUENCE: 43
ucuagcuuua ccuugg                                                     16

<210> SEQ ID NO 44
<211> LENGTH: 16
<212> TYPE: RNA
<213> ORGANISM: Artificial Sequence
<220> FEATURE:
<223> OTHER INFORMATION: anti-sense strand of "Bubbles" dsRNA

<400> SEQUENCE: 44
agaugcuuua ccuacc                                                     16

<210> SEQ ID NO 45
<211> LENGTH: 13
<212> TYPE: RNA

```
<213> ORGANISM: Artificial Sequence
<220> FEATURE:
<223> OTHER INFORMATION: polyadenylated tail at 3' untranslated region
      of multiple double-stranded stem RNA

<400> SEQUENCE: 45
aaaaaaaaaa aaa                                                          13

<210> SEQ ID NO 46
<211> LENGTH: 13
<212> TYPE: RNA
<213> ORGANISM: Artificial Sequence
<220> FEATURE:
<223> OTHER INFORMATION: polyadenylated tail at 3' untranslated region
      of multiple double-stranded stem RNA

<400> SEQUENCE: 46
aaaaaaaaaa aaa                                                          13
```